(12) United States Patent
Fairhurst et al.

(10) Patent No.: US 7,745,462 B2
(45) Date of Patent: Jun. 29, 2010

(54) QUINOLINE-2-ONE DERIVATIVES FOR THE TREATMENT OF AIRWAYS DISEASES

(75) Inventors: Robin Alec Fairhurst, Horsham (GB); David Andrew Sandham, Horsham (GB); David Beattie, Horsham (GB); Ian Bruce, Horsham (GB); Bernard Cuenoud, Lausanne (CH); Reamonn Madden, Portsmouth (GB); Neil John Press, Horsham (GB); Roger John Taylor, Horsham (GB); Katharine Louise Turner, Horsham (GB); Simon James Watson, Horsham (GB)

(73) Assignee: Novartis AG, Basel (CH)

( * ) Notice: Subject to any disclaimer, the term of this patent is extended or adjusted under 35 U.S.C. 154(b) by 913 days.

(21) Appl. No.: 10/552,023

(22) PCT Filed: Apr. 2, 2004

(86) PCT No.: PCT/EP2004/003516

§ 371 (c)(1),
(2), (4) Date: Jul. 27, 2006

(87) PCT Pub. No.: WO2004/087142

PCT Pub. Date: Oct. 14, 2004

(65) Prior Publication Data

US 2007/0066607 A1   Mar. 22, 2007

(30) Foreign Application Priority Data

| Apr. 4, 2003 | (GB) | .................................. 0307856.5 |
| May 19, 2003 | (GB) | .................................. 0311462.6 |
| Jun. 11, 2003 | (GB) | .................................. 0313489.7 |
| Jul. 16, 2003 | (GB) | .................................. 0316656.8 |
| Jul. 16, 2003 | (GB) | .................................. 0316657.6 |

(51) Int. Cl.
*A61K 31/02* (2006.01)
*C07D 215/38* (2006.01)
(52) U.S. Cl. ......................... 514/312; 546/159; 546/162
(58) Field of Classification Search ................... 546/159, 546/162; 514/312
See application file for complete search history.

(56) References Cited

U.S. PATENT DOCUMENTS

| 4,460,581 A | | 7/1984 | Fuegner et al. | |
| 6,800,643 B2 * | | 10/2004 | Cuenoud et al. | ............ 514/312 |
| 6,878,721 B1 * | | 4/2005 | Cuenoud et al. | ............ 514/312 |
| 7,008,951 B2 * | | 3/2006 | Cuenoud et al. | ............ 514/311 |
| 7,250,426 B2 * | | 7/2007 | Konetzki et al. | ............ 514/312 |
| 7,317,102 B2 * | | 1/2008 | Mammen et al. | ............ 546/176 |
| 7,417,051 B2 * | | 8/2008 | Banholzer et al. | ........... 514/291 |
| 7,534,890 B2 * | | 5/2009 | Lohse et al. | ................ 546/167 |

FOREIGN PATENT DOCUMENTS

| EP | 0 073 505 | | 3/1983 |
| GB | 2106105 | | 4/1983 |
| JP | 51149282 A | | 12/1976 |
| WO | 93/18007 | | 9/1993 |
| WO | WO 95/25104 | | 9/1995 |
| WO | 00/75114 | | 12/2000 |
| WO | WO00/75114 | * | 12/2000 |
| WO | 02/45703 | | 6/2002 |
| WO | 02/45703 | * | 6/2009 |

OTHER PUBLICATIONS

Patent Abstracts of Japan, vol. 0010, No. 45 (C-011) (1977) and JP 52 000282, Jan. 5, 1977—Abstract.
Patent Abstracts of Japan, vol. 0062, No. 61 (C-141) (1982) and JP 57 154129, Sep. 22, 1982—Abstract.
Patent Abstracts of Japan, vol. 0082, No. 5 (C-243) (1984) and JP 59 093051, May 29, 1984—Abstract.
Patent Abstracts of Japan, vol. 0082, No. 5 (C-243) (1984) and JP 59 093052, May 29, 1984—Abstract.
Patent Abstracts of Japan, vol. 0092, No. 71 (C-311) (1985) and JP 60 120864, Jun. 28, 1985—Abstract.
Yoshizaki et al., "Sympathomimetic Amines Having a Carbostyril Nucleus", J. Med. Chem., vol. 19, No. 9, pp. 1138-1142 (1976).

* cited by examiner

*Primary Examiner*—D. Margaret Seaman
(74) *Attorney, Agent, or Firm*—Cozette M McAvoy

(57) ABSTRACT

Compounds of formula I

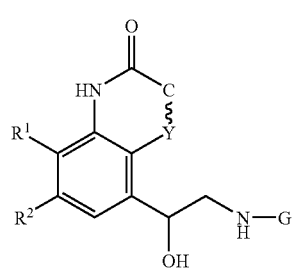

in free or salt form, wherein —C—Y—, $R^1$ and $R^2$ are G have the meanings as indicated in the specification, are useful for treating conditions that are prevented or alleviated by activation of the $\beta_2$-adrenoreceptor. Pharmaceutical compositions that contain the compounds and a process for preparing the compounds are also described.

12 Claims, No Drawings

QUINOLINE-2-ONE DERIVATIVES FOR THE TREATMENT OF AIRWAYS DISEASES

This invention relates to organic compounds, their preparation and use as pharmaceuticals.

The invention provides in one aspect a compound of formula I

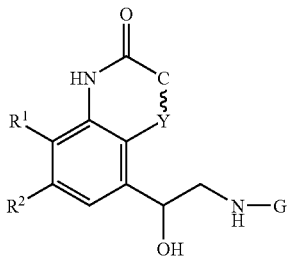

I in free or salt or solvate form, where —C~Y— denotes —CH$_2$—CH$_2$—, —CH=CH— or —CH$_2$—O—;

one of R$^1$ and R$^2$ is hydroxy and the other is hydrogen;

G is a group having the formula Ia, Ib, Ic, Id or Ie

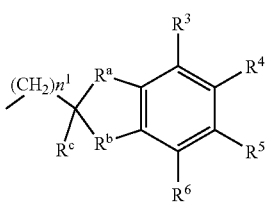

Ia

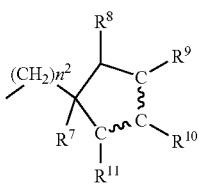

Ib

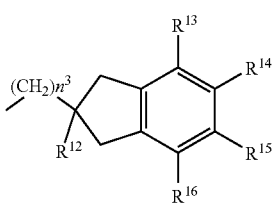

Ic

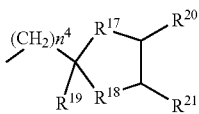

Id

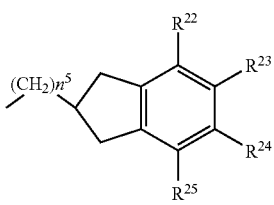

Ie n$^1$ is an integer from 0 to 4;

when n$^1$ is 0, R$^a$ is CR$^{26}$R$^{27}$—, —CH$_2$—CH$_2$—, —CH$_2$—CH$_2$—CH$_2$—, —CH$_2$—O—, —CH$_2$—O—CH$_2$—, —CH$_2$—S—, —CH$_2$—CH$_2$—S—, —CH$_2$—SO—, —CH$_2$—SO$_2$— or a bond, and R$^b$ is —CR$^{28}$R$^{29}$—, —CH$_2$—CH$_2$—, —CH$_2$—O—, —CH$_2$—O—CH$_2$, —CH$_2$—S—, —CH$_2$—CH$_2$—S—, —CH$_2$—SO—, —CH$_2$—SO$_2$— or a bond, otherwise when n$^1$ is 1, 2, 3 or 4, R$^a$ and R$^b$ are independently —CR$^{26}$R$^{27}$—, —CH$_2$—CH$_2$—, —CH$_2$—CH$_2$—CH$_2$—, —O—, —CH$_2$—O—, —CH$_2$—O—CH$_2$—, —S—, —SO—, —SO$_2$—, —CH$_2$—S—, —CH,—CH$_2$—S—, —CH$_2$—SO—, —CH$_2$—SO$_2$— or a bond;

R$^c$ is hydrogen or C$_1$-C$_{10}$-alkyl optionally substituted by a C$_5$-C$_{15}$-carbocyclic group or by C$_1$-C$_{10}$-alkoxy, or when R$^b$ is —CR$^{26}$R$^{27}$ or —CR$^{28}$R$^{29}$—, R$^c$ and R$^b$ form a C$_5$-C$_{15}$-carbocyclic group; R$^3$, R$^4$, R$^5$ and R$^6$ are independently hydrogen, halo, C$_1$-C$_{10}$-alkyl, C$_1$-C$_{10}$-alkoxy, or a 5- or 6-membered heterocyclic ring wherein at least one of the ring atoms is nitrogen, oxygen or sulphur, or any two of R$^3$, R$^4$, R$^5$ and R$^6$ that are attached to adjacent carbon atoms on the phenylene ring together form a phenylene ring, C$_3$-C$_{10}$-cycloalkyl, C$_3$-C$_{10}$-cycloalkenyl or 5- or 6-membered heterocyclic ring wherein at least one of the ring atoms is nitrogen, oxygen or sulphur;

R$^{26}$, R$^{27}$ and R$^{28}$ are independently hydrogen, C$_1$-C$_{10}$-alkyl or C$_1$-C$_{10}$-alkoxy, either of which being optionally substituted by a C$_5$-C$_{15}$-carbocyclic group;

R$^{29}$ is C$_1$-C$_{10}$-alkyl or C$_1$-C$_{10}$-alkoxy, either of which being optionally substituted by a C$_5$-C$_{15}$-carbocyclic group;

n$^2$ is an integer from 0 to 4;

C~C denotes C=C or CH—CH;

R$^7$ is hydrogen or C$_1$-C$_{10}$-alkyl optionally substituted by a C$_3$-C$_{15}$-carbocyclic group or by C$_1$-C$_{10}$-alkoxy;

R$^8$ is hydrogen, hydroxy, C$_1$-C$_{10}$-alkyl or C$_1$-C$_{10}$-alkoxy;

R$^9$ and R$^{10}$ are independently hydrogen, halo, a C$_3$-C$_{15}$-carbocyclic group, a 5- or 6-membered heterocyclic ring wherein at least one of the ring atoms is nitrogen, oxygen or sulphur, C$_1$-C$_{10}$-alkyl optionally substituted by a C$_3$-C$_{15}$-carbocyclic group, or C$_1$-C$_{10}$-alkoxy optionally substituted by a C$_3$-C$_{15}$-carbocyclic group, or R$^9$ and R$^{10}$ together form a C$_3$-C$_{10}$-cycloalkyl or C$_3$-C$_{10}$-cycloalkenyl in either case optionally substituted by C$_1$-C$_{10}$-alkyl or C$_1$-C$_{10}$-alkoxy;

R$^{11}$ is hydrogen, hydroxy, a C$_3$-C$_{15}$-carbocyclic group, C$_1$-C$_{10}$-alkyl optionally substituted by a C$_3$-C$_{15}$-carbocyclic group, or C$_1$-C$_{10}$-alkoxy optionally substituted by a C$_3$-C$_{15}$-carbocyclic group;

n$^3$ is an integer from 0 to 4;

R$^{12}$ is C$_1$-C$_{10}$-alkyl substituted by C$_1$-C$_{10}$-alkoxy, C$_7$-C$_{15}$-aralkyloxy, a C$_5$-C$_{15}$-carbocyclic group or by a 5- or 6-membered heterocyclic ring wherein at least one of the ring atoms is nitrogen, oxygen or sulphur;

R$^{13}$, R$^{14}$, R$^{15}$ and R$^{16}$ are independently hydrogen, halo, cyano, carboxy, nitro, C$_1$-C$_{10}$-alkyl, C$_2$-C$_{10}$-alkenyl, C$_1$-C$_{10}$-alkoxy, C$_7$-C$_{15}$-aralkyloxy, tri-C$_1$-C$_{10}$-alkylsilyl, aminocarbonyl, amino, C$_1$-C$_{10}$-alkylamino, di(C$_1$-C$_{10}$-alkyl)amino, a C$_5$-C$_{15}$-carbocyclic group or a 5- or 6-membered heterocyclic ring wherein at least one of the ring atoms is nitrogen, oxygen or sulphur, or any two of R$^{13}$, R$^{14}$, R$^{15}$ and R$^{16}$ that are attached to adjacent carbon atoms on the benzene ring together with the carbon atoms to which they are attached form a C$_3$-C$_{10}$-cycloaliphatic ring, a 5- or 6-membered heterocyclic ring wherein at least one of the ring atoms is nitrogen, oxygen or sulphur, or a benzene ring optionally substituted by halo, cyano, hydroxy, carboxy, aminocarbonyl, nitro, C$_1$-C$_{10}$-alkyl, C$_1$-C$_{10}$-alkoxy or C$_3$-C$_{10}$-cycloalkyl;

$n^4$ is an integer from 0 to 4;

$R^{17}$ and $R^{18}$ are independently —$CR^{30}R^{31}$—, —$CH_2$—$CH_2$—, —$CH_2$—$CH_2$—$CH_2$—, —O—, —$CH_2$—O—, —$CH_2$—O—$CH_2$—, —S—, —SO—, —$SO_2$—, —$CH_2$—S—, —$CH_2$—$CH_2$—S—, —$CH_2$—SO—, —$CH_2$—$SO_2$— or a bond;

$R^{19}$ is hydrogen or $C_1$-$C_{10}$-alkyl optionally substituted by $C_1$-$C_{10}$-alkoxy, $C_7$-$C_{15}$-aralkyloxy, a $C_5$-$C_{15}$-carbocyclic group or by a 5- or 6-membered heterocyclic group wherein at least one of the ring atoms is nitrogen, oxygen or sulphur;

or when $R^{18}$ is —$CR^{30}R^{31}$—, $R^{19}$ and $R^{18}$ form a $C_5$-$C_{15}$-carbocyclic group;

$R^{20}$ and $R^{21}$ form a 5- or 6-membered heterocyclic ring wherein at least one of the ring atoms is nitrogen, oxygen or sulphur, that ring being optionally substituted by halo, oxo, cyano, hydroxy, carboxy, aminocarbonyl, nitro, a $C_5$-$C_{15}$-carbocyclic group, $C_7$-$C_{15}$-aralkyl, $C_1$-$C_{10}$-alkyl optionally substituted by $C_3$-$C_{10}$-cycloalkyl, or $C_1$-$C_{10}$-alkoxy optionally substituted by $C_3$-$C_{10}$-cycloalkyl;

$R^{30}$ and $R^{31}$ are independently hydrogen, $C_1$-$C_{10}$-alkyl or $C_1$-$C_{10}$-alkoxy, either of which being optionally substituted by a $C_5$-$C_{15}$-carbocyclic group;

$n^5$ is an integer from 0 to 4; and at least one of $R^{22}$, $R^{23}$, $R^{24}$ and $R^{25}$ s is a 5- to 12-membered heterocyclic ring wherein at least one of the ring atoms is nitrogen, oxygen or sulphur, that ring being optionally and independently substituted by halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl, the other or others of $R^{22}$, $R^{23}$, $R^{24}$ and $R^{25}$ being independently hydrogen, halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl.

Terms used in this specification have the following meanings:

"Substituted" as used herein means the group referred to can be substituted at one or more positions by any one or any combination of the radicals listed thereafter.

"Optionally substituted" as used herein means the group referred to can be substituted at one or more positions by any one or any combination of the radicals listed thereafter.

"Optionally and independently substituted" as used herein means where there are two or more moieties that may be optionally substituted as herein defined those moieties may be similarly or differently substituted.

"$C_1$-$C_{10}$-alkyl" as used herein denotes straight chain or branched alkyl having 1 to 10 carbon atoms. Preferably $C_1$-$C_{10}$-alkyl is $C_1$-$C_4$-alkyl.

"$C_1$-$C_{10}$-alkoxy" as used herein denotes straight chain or branched alkoxy having 1 to 10 carbon atoms. Preferably $C_1$-$C_{10}$-alkoxy is $C_1$-$C_6$-alkoxy.

"$C_3$-$C_{10}$-cycloalkyl" as used herein denotes cycloalkyl having 3 to 10 ring carbon atoms, for example a monocyclic group such as a cyclopropyl, cyclobutyl, cyclopentyl, cyclohexyl, cycloheptyl, cyclooctyl, cyclononyl or cyclodecyl, any of which can be substituted by one or more, usually one or two, $C_1$-$C_4$-alkyl groups, or a bicyclic group such as bicycloheptyl or bicyclooctyl. Preferably $C_3$-$C_{10}$-cycloalkyl is $C_3$-$C_6$-cycloalkyl, for example cyclopropyl, cyclobutyl, cyclopentyl or cyclohexyl.

"$C_1$-$C_{10}$-alkylene" as used herein denotes straight chain or branched alkylene having 1 to 10 carbon atoms. Preferably $C_1$-$C_{10}$-alkylene is $C_1$-$C_4$-alkylene. 5"$C_2$-$C_{10}$-alkenyl" as used herein denotes straight chain or branched hydrocarbon chains that contain 2 to 10 carbon atoms and one or more carbon-carbon double bonds. Preferably "$C_2$-$C_{10}$-alkenyl" is "$C_2$-$C_4$-alkenyl".

"$C_3$-$C_{10}$-cycloalkenyl" as used herein denotes a monovalent hydrocarbon cyclic group that contains 3 to 10 ring carbon atoms and at least one but no more than two carbon-carbon double bonds, for example a monocyclic group such as a cyclopropenyl, cyclobutenyl, cyclopentenyl, cyclohexenyl, cycloheptenyl, cyclooctenyl, cyclononenyl or cyclodecenyl, any of which can be substituted by one or more, usually one or two, $C_1$-$C_4$-alkyl groups, or a bicyclic group such as bicyclohexenyl, bicycloheptenyl, bicyclooctenyl, bicyclononenyl or bicyclodecenyl. Preferably $C_3$-$C_{10}$-cycloalkenyl is $C_3$-$C_6$-cycloalkenyl, for example cyclopropenyl, cyclobutenyl, cyclopentenyl or cyclohexenyl.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is $C_6$-$C_8$-aryl, especially phenyl.

"$C_7$-$C_{15}$-aralkyl" as used herein denotes alkyl, for example $C_1$-$C_5$-alkyl as hereinbefore defined, substituted by $C_6$-$C_{10}$-aryl as hereinbefore defined. Preferably $C_7$-$C_{15}$-aralkyl is $C_7$-$C_{10}$-aralkyl such as phenyl-$C_1$-$C_4$-alkyl, but especially benzyl.

"$C_7$-$C_{15}$-aralkylene" as used herein denotes alkylene, for example $C_1$-$C_5$-alkylene as hereinbefore defined, substituted by $C_6$-$C_{10}$-aryl as hereinbefore defined. Preferably $C_7$-$C_{15}$-aralkylene is $C_7$-$C_{10}$-aralkylene such as phenyl-$C_1$-$C_4$-alkylene.

"$C_7$-$C_{15}$-aralkyloxy" as used herein denotes alkoxy, for example $C_1$-$C_5$-alkoxy as hereinbefore defined, substituted by $C_6$-$C_{10}$-aryl as hereinbefore defined. Preferably $C_7$-$C_{15}$-aralkyloky is $C_7$-$C_{10}$-aralkyloxy such as phenyl-$C_1$-$C_4$-alkoxy, particularly benzyloxy.

"$C_3$-$C_{10}$-cycloaliphatic ring" as used herein denotes a cycloaliphatic ring having 3 to 10 ring carbon atoms, for example a $C_3$-$C_{10}$-cycloalkyl as hereinbefore defined or a $C_3$-$C_{10}$-cycloalkenyl".

"$C_3$-$C_{15}$-carbocyclic group" as used herein denotes a carbocyclic group having 3 to 15 ring carbon atoms, for example a monocyclic group, either aromatic or non-aromatic, such as a cyclopropyl, cyclobutyl, cyclopentyl, cyclohexyl, cycloheptyl, cyclooctyl or phenyl, any of which can be substituted by one or more, usually one or two, $C_1$-$C_4$-alkyl groups, or a bicyclic group such as bicyclooctyl, bicyclononyl, bicyclodecyl, indanyl or indenyl, again any of which can be substituted by one or more, usually one or two, $C_1$-$C_4$-alkyl groups. Preferably the $C_3$-$C_{15}$-carbocyclic group is a $C_5$-$C_{10}$-carbocyclic group, especially for example cyclopentyl, cyclohexyl or phenyl.

"$C_5$-$C_{15}$-carbocyclic group" as used herein denotes a carbocyclic group having 5 to 15 ring carbon atoms, for example a monocyclic group, either aromatic or non-aromatic, such as a cyclopentyl, cyclohexyl, cycloheptyl, cyclooctyl or phenyl, or a bicyclic group such as bicyclooctyl, bicyclononyl, bicyclodecyl, indanyl or indenyl, again any of which can be substituted by one or more, usually one or two, $C_1$-$C_4$-alkyl groups. Preferably the $C_5$-$C_{15}$-carbocyclic group is a $C_5$-$C_{10}$-carbocyclic group, especially phenyl, cyclohexyl or indanyl. The $C_5$-$C_{15}$-carbocyclic group can substituted can be unsubstituted or substituted. Preferred substituents on the heterocyclic ring include halo, cyano, hydroxy, carboxy, aminocarbonyl, nitro, $C_1$-$C_{10}$-alkyl, $C_1$-$C_{10}$-alkoxy and $C_3$-$C_{10}$-cycloalkyl. When the $C_5$-$C_{15}$-carbocyclic group is phenyl it is most preferably unsubstituted or substituted by either $C_1$-$C_{10}$-alkyl especially methyl or $C_1$-$C_4$-alkoxy especially methoxy.

"Halo" or "halogen" as used herein denotes a element belonging to group 17 (formerly group VII) of the Periodic Table of Elements, which may be, for example, fluorine, chlorine, bromine or iodine. Preferably halo or halogen is fluorine, chlorine or bromine.

"Halo-$C_1$-$C_{10}$-alkyl" as used herein denotes $C_1$-$C_{10}$-alkyl as hereinbefore defined substituted by one or more halogen atoms, preferably one, two or three halogen atoms. Preferably halo-$C_1$-$C_{10}$-alkyl is fluoro-$C_1$-$C_{10}$-alkyl, especially trifluoromethyl.

"Tri-$C_1$-$C_{10}$-alkylsilyl" as used herein denotes silyl substituted by three $C_1$-$C_{10}$-alkyl groups as hereinbefore defined.

"Aminocarbonyl" as used herein denotes amino attached through the nitrogen atom to a carbonyl group.

"$C_1$-$C_{10}$-alkylamino" and "di($C_1$-$C_{10}$-alkyl)amino" as used herein denote amino substituted respectively by one or two $C_1$-$C_{10}$-alkyl groups as hereinbefore defined, which may be the same or different. Preferably $C_1$-$C_{10}$-alkylamino and di($C_1$-$C_{10}$-alkyl)amino are respectively $C_1$-$C_4$-alkylamino and di($C_1$-$C_4$-alkyl)amino.

"5- or 6-membered heterocyclic ring containing at least one ring heteroatom selected from the group consisting of nitrogen, oxygen and sulphur" as used herein may be, for example, pyrrole, pyrrolidine, pyrazole, imidazole, triazole, tetrazole, furan, thiadiazole, thiazole, isothiazole, thiophene, oxadiazole, pyridine, oxazole, isoxazole, pyrazine, pyridazine, pyrimidine, piperazine, morpholino, triazine, oxazine or thiazine. Preferred 5- or 6-membered heterocyclic rings include furan, thiazole, pyridine, pyrrolidine, pyrrole, pyrazole, imidazole, furan, thiophene and pyrazine. The 5- or 6-membered heterocyclic ring can be unsubstituted or substituted. Preferred substituents on the heterocyclic ring include halo, cyano, hydroxy, carboxy, aminocarbonyl, nitro, $C_1$-$C_{10}$-alkyl, $C_1$-$C_{10}$-alkoxy and $C_3$-$C_{10}$-cycloalkyl. Especially preferred substituents on the ring include oxo, $C_1$-$C_{10}$-alkoxy, $C_7$-$C_{15}$-aralkyl and $C_1$-$C_{10}$-alkyl optionally substituted by $C_3$-$C_{10}$-cycloalkyl. When the 5- or 6-membered heterocyclic ring is a substituent on the benzo ring of the indanyl group of the compound of formula I it is preferably unsubstituted pyridyl or it is furanyl or thiazolyl substituted by either halo or $C_1$-$C_4$-alkyl.

"5- to 12-membered heterocyclic ring containing at least one ring heteroatom selected from nitrogen, oxygen and sulphur" as used herein denotes a monoheterocyclic, biheterocyclic or triheterocyclic group, which may be saturated or unsaturated, that has 5 to 12 ring atoms. Monoheterocyclic rings include furan, pyrrole, pyrrolidine, pyrazole, imidazole, triazole, tetrazole, thiophene, thiadiazole, isothiazole, oxadiazole, pyridine, oxazole, isoxazole, piperidine, pyridine, pyrazine, pyridazine, pyrimidine, piperazine, morpholine, triazine, oxazine, thiazole, thiadiazole or tetrazole. Biheterocyclic rings include benzazole, indole, benzimidazole, indazole, benzothiophene and benzothiazole. Preferably the 5- to 12-membered heterocyclic ring containing at least one ring heteroatom selected from nitrogen, oxygen and sulphur is a 5- to 9-membered heterocyclic ring containing at least one ring heteroatom selected from nitrogen, oxygen and sulphur. Preferred 5- to 12-membered heterocyclic rings include furan, thiophene, pyridine, thiazole, thiadiazole, tetrazole and benzothiophene. The 5- to 12-membered heterocyclic ring can be unsubstituted or substituted. Preferred substituents on the heterocyclic ring include halo, cyano, hydroxy, carboxy, aminocarbonyl, nitro, $C_1$-$C_{10}$-alkyl, $C_1$-$C_{10}$-alkoxy and $C_3$-$C_{10}$-cycloalkyl. Especially preferred substituents are halo and $C_1$-$C_{10}$-alkyl.

When any two of $R^3$, $R^4$, $R^5$ and $R^6$ in formula 1a or any two of $R^{13}$, $R^{14}$, $R^{15}$ and $R^{16}$ in formula 1c that are attached to adjacent carbon atoms on the phenylene ring together form a phenylene ring, that ring so formed can be unsubstituted or substituted. Preferred substituents on that ring include halo, cyano, hydroxy, carboxy, aminocarbonyl, nitro, $C_1$-$C_{10}$-alkyl, $C_1$-$C_{10}$-alkoxy and $C_3$-$C_{10}$-cycloalkyl. Especially preferred substituents on the ring include $C_1$-$C_{10}$-alkyl and $C_1$-$C_{10}$-alkoxy.

"C~C" denotes C=C or CH—CH. However in order to observe the maximum valence permitted "C~C~C" can be "C—C—C", "C—C=C" or "C=C—C" but not "C=C=C".

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of the present invention are compounds of formula I where —C~Y— is —CH=CH—;

$R^1$ is hydroxy and $R^2$ is hydrogen;

G is a group having the formula Ia, Ib, Ic, Id or Ie;

$n^1$ is 0 or 1;

when $n^1$ is 0, $R^a$ is —$CR^{26}R^{27}$—, —$CH_2$—$CH_2$—, —$CH_2$—$CH_2$—$CH_2$—, —$CH_2$—O—$CH_2$— or —$CH_2$—$CH_2$—S—, and $R^b$ is —$CR_{28}R_{29}$—, —$CH_2$—O— or a bond, otherwise when $n^1$ is 1, $R^a$ and $R^b$ are both —$CR^{26}R^{27}$—;

$R^c$ is hydrogen or $C_1$-$C_{10}$-alkyl optionally substituted by a $C_5$-$C_{15}$-carbocyclic group or by $C_1$-$C_{10}$-alkoxy, or when $R^b$ is —$CR^{26}R^{27}$— or —$CR^{28}R^{29}$—, $R^c$ and $R^b$ form a $C_5$-$C_{15}$-carbocyclic group;

$R^3$, $R^4$, $R^5$ and $R^6$ are independently hydrogen, $C_1$-$C_{10}$-alkyl or $C_1$-$C_{10}$-alkoxy;

$R^{26}$, $R^{27}$ and $R^{28}$ are independently hydrogen, $C_1$-$C_{10}$-alkyl, $C_1$-$C_{10}$-alkoxy or a 5- or 6-membered heterocyclic ring wherein at least one of the ring atoms is nitrogen, oxygen or sulphur;

$R^{29}$ is $C_1$-$C_{10}$-alkyl or $C_1$-$C_{10}$-alkoxy;

$n^2$ is 0;

C~C denotes C=C or CH—CH;

$R^7$ and $R^8$ are both hydrogen;

$R^9$ and $R^{10}$ are independently hydrogen or $C_1$-$C_{10}$-alkyl, or $R^9$ and $R^{10}$ together form a $C_3$-$C_{10}$-cycloalkyl or $C_3$-$C_{10}$-cycloalkenyl in either case optionally substituted by $C_1$-$C_{10}$-alkyl;

$R^{11}$ is hydrogen, hydroxy, a $C_3$-$C_{15}$-carbocyclic group or $C_1$-$C_{10}$-alkyl optionally substituted by a $C_3$-$C_{15}$-carbocyclic group;

$n^3$ is 0;

$R^{12}$ is $C_1$-$C_{10}$-alkyl substituted by $C_1$-$C_{10}$-alkoxy, $C_7$-$C_{15}$-aralkyloxy or by a $C_5$-$C_{15}$-carbocyclic group;

$R^{13}$, $R^{14}$, $R^{15}$ and $R^{16}$ are independently hydrogen or $C_1$-$C_{10}$-alkyl;

$n^4$ is 0 or 1;

$R^{17}$ and $R^{18}$ are both methylene;

$R^{19}$ is hydrogen;

$R^{20}$ and $R^{21}$ form a 5- or 6-membered heterocyclic ring wherein at least one of the ring atoms is nitrogen, oxygen or sulphur, that ring being optionally substituted by oxo, $C_7$-$C_{15}$-aralkyl or $C_1$-$C_{10}$-alkyl optionally substituted by $C_3$-$C_{10}$-cycloalkyl;

$n^5$ is 0; and at least one of $R^{22}$, $R^{23}$, $R^{24}$ and $R^{25}$ is a 5- to 12-membered heterocyclic ring wherein at least one of the ring atoms is nitrogen, oxygen or sulphur, that ring being optionally and independently substituted by halo or $C_1$-$C_{10}$-alkyl, the other or others of $R^{22}$, $R^{23}$, $R^{24}$ and $R^{25}$ being hydrogen.

Especially preferred compounds of the present invention are compounds of formula I where —C~Y— is —CH=CH—;

$R^1$ is hydroxy and $R^2$ is hydrogen;
$n^1$ is 0 or 1;
when $n^1$ is 0, $R^a$ is —$CR^{26}R^{27}$—, —$CH_2$—$CH_2$—, —$CH_2$—$CH_2$—$CH_2$—, —$CH_2$—O—$CH_2$— or —$CH_2$—$CH_2$—S—, and $R^b$ is —$CR^{28}R^{29}$—, —$CH_2$—O— or a bond, otherwise when $n^1$ is 1, $R^a$ and $R^b$ are both —$CR^{26}R^{27}$—;
$R^c$ is hydrogen or $C_1$-$C_4$-alkyl optionally substituted by a $C_5$-$C_{10}$-carbocyclic group or by $C_1$-$C_4$-alkoxy,
or when $R^b$ is —$CR^{26}R^{27}$— or —$CR^{28}R^{29}$—, $R^c$ and $R^b$ form a $C_5$-$C_{10}$-carbocyclic group;
$R^3$, $R^4$, $R^5$ and $R^6$ are independently hydrogen, $C_1$-$C_4$-alkyl or $C_1$-$C_4$-alkoxy;
$R^{25}$, $R^{27}$ and $R^{28}$ are independently hydrogen, $C_1$-$C_4$-alkyl, $C_1$-$C_4$-alkoxy or a 5— or 6-membered heterocyclic ring wherein at least one of the ring atoms is nitrogen, oxygen or sulphur;
$R^{29}$ is $C_1$-$C_4$-alkyl or $C_1$-$C_4$-alkoxy;
$n^2$ is 0;
C~C denotes C=C or CH—CH;
$R^7$ and $R^8$ are both hydrogen;
$R^9$ and $R^{10}$ are independently hydrogen or $C_1$-$C_4$-alkyl, or $R^5$ and $R^6$ together form a $C_3$-$C_6$-cycloalkyl or $C_3$-$C_6$-cycloalkenyl in either case optionally substituted by $C_1$-$C_4$-alkyl;
$R^{11}$ is hydrogen, hydroxy, a $C_3$-$C_{10}$-carbocyclic preferably $C_3$-$C_6$-cycloalkyl, or $C_1$-$C_{10}$-alkyl optionally substituted by a $C_3$-$C_{10}$-carbocyclic group preferably an unsaturated $C_5$-$C_8$-carbocyclic group;
$n^3$ is 0;
$R^{12}$ is $C_1$-$C_{14}$-alkyl substituted by $C_1$-$C_6$-alkoxy, $C_7$-$C_{10}$-aralkyloxy or by a $C_5$-$C_{10}$-carbocyclic group;
$R^{13}$ and $R^{16}$ are both hydrogen;
$R^{14}$ and $R^{15}$ are independently hydrogen or $C_1$-$C_4$-alkyl.
$n^4$ is 0 or 1;
$R^{17}$ and $R^{18}$ are both methylene;
$R^{19}$ is hydrogen;
$R^{20}$ and $R^{21}$ form a 5- or 6-membered heterocyclic ring wherein at least one of the ring atoms is nitrogen, oxygen or sulphur, that ring being optionally substituted by oxo, $C_7$-$C_{10}$-aralkyl or $C_1$-$C_4$-alkyl optionally substituted by $C_3$-$C_6$-cycloalkyl.
$n^5$ is 0; and
at least one of $R^{22}$, $R^{23}$, $R^{24}$ and $R^{25}$ is a 5- to 9-membered heterocyclic ring wherein at least one of the ring atoms is nitrogen, oxygen or sulphur, that ring being optionally and independently substituted by halo or $C_1$-$C_4$-alkyl,
the other or others of $R^{22}$, $R^{23}$, $R^{24}$ and $R^{25}$ being hydrogen.

The compounds of formula (I) are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids such as formic acid, acetic acid, propionic acid, butyric acid, benzoic acid, o-hydroxybenzoic acid, p-hydroxybenzoic acid, p-chlorobenzoic acid, diphenylacetic acid, triphenylacetic acid, 1-hydroxynaphthalene-2-carboxylic acid, 3-hydroxynaphthalene-2-carboxylic acid, aliphatic hydroxy acids such as lactic acid, citric acid, tartaric acid or malic acid, dicarboxylic acids such as fumaric acid, maleic acid or succinic acid and sulfonic acids such as methanesulfonic acid or benzenesulfonic acid, and unsaturated monobasic aromatic acids such cinnamic acid, 4-methoxy cinnamic acid or 4-methyl cinnamic acid. These salts may be prepared from compounds of formula I by known salt-forming procedures.

Compounds of formula I which contain acidic, e.g. carboxyl groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces individual optically active R and S isomers as well as mixtures, e.g. racemic or diastereomeric mixtures, thereof. Specific especially preferred compounds of the invention are those described hereinafter in the Examples.

The present invention also provides a process for the preparation of compounds of formula I in free or salt or solvate form. They can be prepared by a process comprising:

(i) (A) reacting a compound of formula II

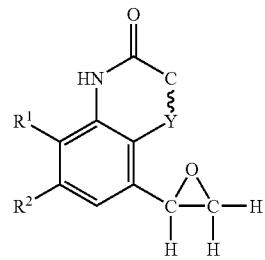

II or a protected form thereof wherein —C—Y—, $R^1$ and $R^2$ are as hereinbefore defined, with a compound of formula III $H_2N$-G    III where G is a group of formula Ia, Ib, Ic, Id or Ie

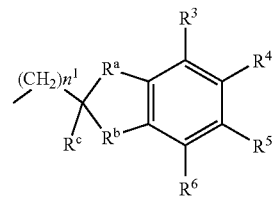

Ia

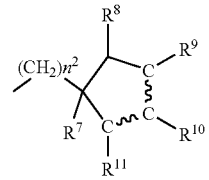

Ib

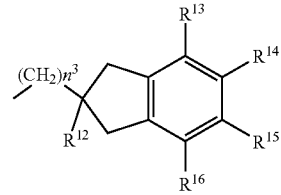

Ic

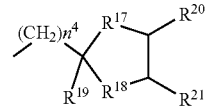

Id

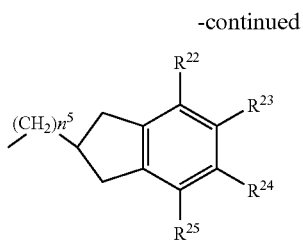

or a protected form thereof wherein $n^1$, $n^2$, $n^3$, $n^4$, $n^5$, $R^a$, $R^b$, $R^c$ and $R^3$ through $R^{25}$ are as hereinbefore defined; or (B) reducing a compound of formula IV

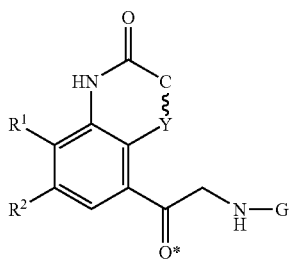

or a protected form thereof wherein —C—Y—, $R^1$, $R^2$ and G are as hereinbefore defined, to convert the indicated keto group into —CH(OH); or (C) for the preparation of compounds of formula I where G is a group of formula Ia, $R^c$ is hydrogen and $n^1$ is 0, reacting a compound of formula V

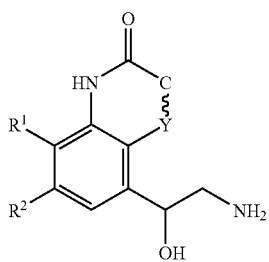

or a protected form thereof wherein —C~Y—, $R^1$ and $R^2$ are as hereinbefore defined, with a compound of formula VI

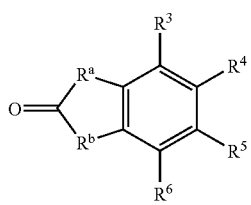

or a protected form thereof wherein $R^a$, $R^b$, $R^3$, $R^4$, $R^5$ and $R^6$ are as hereinbefore defined; or (D) for the preparation of compounds of formula I where G is a group of formula 1d, $R^{19}$ is hydrogen and $n^4$ is 0, reacting a compound of formula V or a protected form thereof wherein —C~Y—, $R^1$ and $R^2$ are as hereinbefore defined, with a compound of formula VII

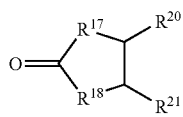

or a protected form thereof wherein $R^{17}$, $R^{18}$, $R^{20}$ and $R^{21}$ are as hereinbefore defined; and (ii) recovering the resultant compound of formula I in free or salt or solvate form.

Process variant (A) may be carried out using known procedures for reacting epoxides with amines or analogously as hereinafter described in the Examples. The reaction is conveniently carried out without a solvent or in an inert solvent, for example an organic solvent such as 2-methoxyethyl ether or N,N'-dimethylformamide in the presence of a silylating agent such as N,O-bis(trimethylsilyl)acetamide. The reaction temperature is conveniently from 25° C. to 200° C., preferably from 80° C. to 190° C. The temperature may be achieved by conventional heating or by microwave irradiation.

Process variant (B) may be carried out using conventional methods, for example by hydrogenation using a suitable catalyst such as Pd/C or by reaction with sodium borohydride or a borane reducing agent under conventional conditions.

Process variants (C) and (D) may be carried out using known procedures for reacting amino alcohols with ketones or analogously under reductive arination conditions as hereinafter described in the Examples. The reaction is conveniently carried out using a borohydride salt under acidic conditions, for example sodium triacetoxyborohydride and acetic acid, and using an organic solvent, for example 1,2-dichloroethane, as described in *J. Org. Chem.* 1996, 61, 3849. The reaction temperature is conveniently from 0° C. to 25° C., preferably room temperature.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Compounds of formula II are known compounds or can be prepared by processes analogous to those used for the preparation of the known compounds, for example the procedures described in *J. Med. Chem.* 1987, 30, 1563.

Compounds of formula II in which the carbon atom of the epoxide ring that is attached to the phenyl group is chiral may be prepared from a compound of formula VIII

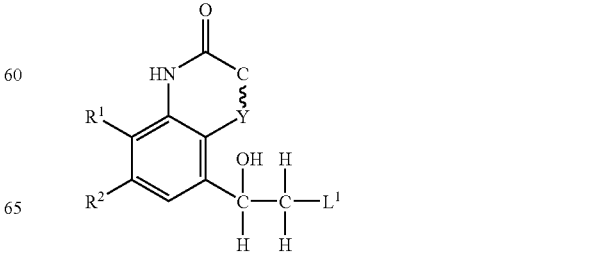

or a protected form thereof where —C~Y—, $R^1$ and $R^2$ are as hereinbefore defined and $L^1$ is a leaving atom or group, as described in international patent application WO 95/25104 or analogously as hereinafter described in the Examples.

Compounds of formula II may alternatively be prepared by epoxidation of a compound of formula IX

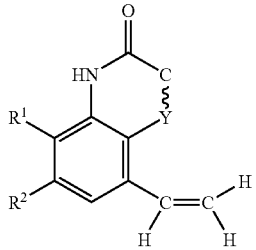

or a protected form thereof —C~Y—, $R^1$ and $R^2$ are as hereinbefore defined, using conventional procedures.

Compounds of formula III are known or may be prepared by methods analogous to those used for the preparation of the known compounds. The amine group may be protected by known methods, for example using an amine-protective group described in Protective Groups in Organic Synthesis, T. W. Greene, P. G. M. Wuts, John Wiley & Sons Inc, Third Edition, 1999, preferably benzyl or trifluoroacetyl.

Compounds of formula III where G is a group of formula 1a as hereinbefore defined and $R^3$ and $R^6$ are hydrogen can be prepared by reacting a compound of formula X

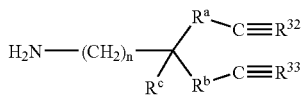

where $R^a$, $R^b$, $R^c$ and $n^1$ are as hereinbefore defined and $R^{32}$ and $R^{33}$ are each independently hydrogen or $C_1$-$C_{10}$-alkyl, with a compound of formula XI

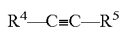

where $R^4$ and $R^5$ are as hereinbefore defined. The reaction may be carried out using known procedures, for example as described in international patent application WO 96/23760 or analogously as hereinafter described in the Examples. The reaction is conveniently carried out in an inert solvent, for example ethanol, preferably in the presence of a catalyst such as tris(triphenylphosphine)rhodium chloride. The reaction temperature is conveniently from 60 to 120° C., preferably from 80 to 100° C. Where $R^4$ and $R^5$ are trialkylsilyl, the reaction between the compounds of formulae X and XI may be carried out in the presence of a metal carbonyl complex catalyst, for example using the procedure described by K. P. C. Vollhardt and R. Hillard, *J. Am. Chem. Soc.* 1977, 99, 4058.

Compounds of formula III where G is a group of formula 1a as hereinbefore defined and $R^c$ is $C_1$-$C_{10}$-alkyl optionally substituted by a $C_5$-$C_{15}$-carbocyclic group or by $C_1$-$C_{10}$-alkoxy, and $R^b$ and $R^c$ are both methylene may be prepared by amination of the corresponding 2-alkyl-indan-1-one using ammonia and $K_3Fe(CN)_6$, for example using the procedure described in Farnum and Carlson, *Synthesis* 1972, 191, or analogously as hereinafter described in the Examples.

Compounds of formula III where G is a group of formula Ic as hereinbefore defined and $R^{13}$ and $R^{16}$ are hydrogen can be prepared by reacting a compound of formula XII

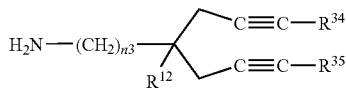

where $R^{12}$ and $n^3$ are as hereinbefore defined and $R^{34}$ and $R^{35}$ are each independently hydrogen or $C_1$-$C_{10}$-alkyl, with a compound of formula XIII

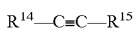

where $R^{14}$ and $R^{15}$ are as hereinbefore defined. The reaction may be carried out using known procedures, for example as described in international patent application WO 96/23760 or analogously as hereinafter described in the Examples. The reaction is conveniently carried out in an inert solvent, for example ethanol, preferably in the presence of a catalyst such as tris(triphenylphosphine)rhodium chloride. The reaction temperature is conveniently from 60 to 120° C., preferably from 80 to 100° C. Where $R^{14}$ and $R^{15}$ are trialkylsilyl, the reaction between the compounds of formulae XII and XIII may be carried out in the presence of a metal carbonyl complex catalyst, for example using the procedure described by K. P. C. Vollhardt and R. Hillard, *J. Am. Chem. Soc.* 1977, 99, 4058.

Compounds of formula III where G is a group of formula Ic as hereinbefore defined and $n^3$ is 0 may be prepared by amination of the corresponding 2-alkyl-indan-1-one using ammonia and potassium hexacyanoferrate ($K_3Fe(CN)_6$), for example using the procedure described in Farnum and Carlson, *Synthesis* 1972, 191, followed by reduction of the keto group or analogously as hereinafter described in the Examples.

Compounds of formula III where G is a group of formula 1c as hereinbefore defined and $R^{12}$ is $C_1$-$C_{10}$-alkyl substituted by $C_1$-$C_{10}$-alkoxy or $C_7$-$C_{15}$-aralkyloxy may be prepared by deprotecting a compound of formula XIV

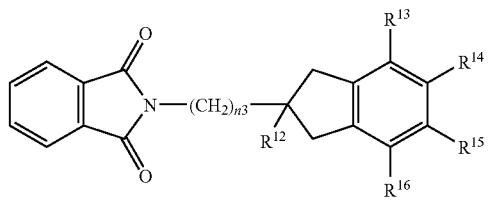

where $R^{12}$, $R^{13}$, $R^{14}$, $R^{15}$, $R^{16}$ and $n^3$ are as hereinbefore defined. The reaction may be carried out using conventional procedures, for example by refluxing hydrazine hydrate in an organic solvent such as ethanol, or analogously as hereinafter described in the Examples.

Compounds of formula III where G is a group of formula Ic as hereinbefore defined and $R^{12}$ is $C_1$-$C_{10}$-alkyl substituted by a $C_5$-$C_{15}$-carbocyclic group may be prepared by reducing a compound of formula XV

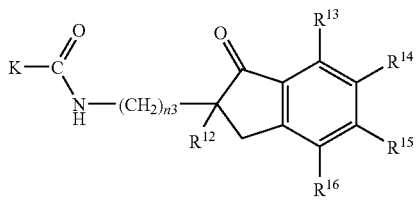

XV

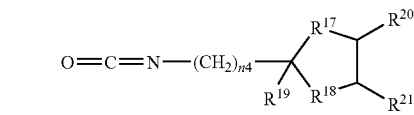

XVII or a protected form thereof wherein $R^{17}$, $R^{18}$, $R^{19}$, $R^{20}$, $R^{21}$ and $n^4$ are as hereinbefore defined, where $R^{12}$, $R^{13}$, $R^{14}$, $R^{15}$, $R^{16}$ and $n^3$ are as hereinbefore defined and K is a halo-$C_1$-$C_8$-alkyl, especially, for example trifluoromethyl. The reaction may be carried out using known procedures, for example using the procedure described in "Advanced Organic Chemistry", J. March, Wiley, 4$^{th}$ edition 1992, page 1209, or analogously as hereinafter described in the Examples.

Compounds of formula III where G is a group of formula 1d as hereinbefore defined may be prepared by methods analogous to those used for the preparation of the known compounds, for example the procedures described by R. Helmers in *J. fuer Practische Chemie*, 1971, 313, 31; M. H. Palmer et al in *Tetrahedron* 1978, 34, 1015; and J. G. Berger et al in *J. Org. Chem.* 1970, 35, 3122. The amine group may be protected by known methods, for example using an amine-protective group described in Protective Groups in Organic Synthesis, T. W. Greene, P. G. M. Wuts, John Wiley & Sons Inc, Third Edition, 1999, preferably benzyl or trifluoroacetyl.

Compounds of formula III where G is a group of formula 1d as hereinbefore defined and $R^{20}$ and $R^{21}$ form a pyrrolidine ring, $R^{19}$ is hydrogen and $n^4$ is 0 may be prepared by reacting a compound of formula XVI

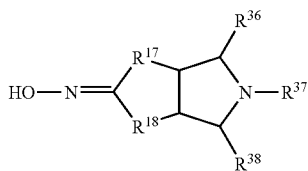

XVI or a protected form thereof where $R^{17}$ and $R^{18}$ are as hereinbefore defined and $R^{36}$, $R^{37}$ and $R^{38}$ are each independently hydrogen, halo, oxo, cyano, hydroxy, carboxy, aminocarbonyl, nitro, a $C_5$-$C_{15}$-carbocyclic group, $C_7$-$C_{15}$-aralkyl, $C_1$-$C_{10}$-alkyl optionally substituted by $C_3$-$C_{10}$-cycloalkyl, or $C_1$-$C_{10}$-alkoxy optionally substituted by $C_3$-$C_{10}$-cycloalky or $C_1$-$C_{10}$-alkyl, with a reducing agent. The reaction may be carried out using known procedures for converting oximes to amines, for example as described by Fischer et al in *J. Het. Chem.* 1991, 28, 1677 or analogously as hereinafter described in the Examples. The reaction is conveniently carried out by hydrogenation in an inert solvent, for example ethanol, preferably in the presence of an acid such as hydrochloric acid and a noble metal catalyst such as platinum oxide. The reaction temperature is conveniently from 0 to 100° C., preferably from 25 to 40° C.

Compounds of formula III where G is a group of formula 1d as hereinbefore defined and $R^{20}$ and $R^{21}$ form a 5- or 6-membered heterocyclic ring may be prepared by reacting a compound of formula XVII with a strong acid in aqueous solution. The reaction may be carried out using known procedures for converting isocyanates to amines, for example as described by Huebner et al in *J. Org. Chem.* 1962, 27, 4465 or analogously as hereinafter described in the Examples. The reaction is conveniently from 80° C. to reflux temperature.

Compounds of formula III where G is a group of formula 1e as hereinbefore defined and $R^{23}$ is a 5- to 12-membered heterocyclic ring wherein at least one of the ring atoms is nitrogen, oxygen or sulphur, that ring being optionally substituted by halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl, and $R^{22}$, $R^{24}$ and $R^{25}$ are hydrogen, can be prepared by reacting a compound of formula XVIII

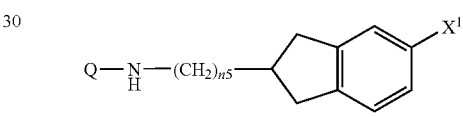

XVIII where $n^5$ is as hereinbefore herein defined, $X^1$ is a halogen such as bromine and Q is an amine-protecting group such as a tertiary-butyloxy-carbonyl group, with a compound of formula XIX

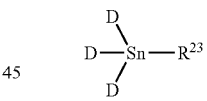

XIX where $R^{23}$ is a 5- to 12-membered heterocyclic ring wherein at least one of the ring atoms is nitrogen, oxygen or sulphur, that ring being optionally substituted by halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl and D is $C_1$-$C_{10}$-alkyl, for example butyl. The reaction can be carried out using the procedure described in *J. Am. Chem. Soc.* 2001, 123, 5918, or analogously as hereinafter described in the Examples. The reaction temperature is conveniently from 80° C. to reflux temperature.

Alternatively, compounds of formula III where G is a group of formula 1e as hereinbefore defined and at least one of $R^{23}$ and $R^{24}$ is a 5- to 12-membered heterocyclic ring wherein at least one of the ring atoms is nitrogen, oxygen or sulphur, that ring being optionally substituted by halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl, and the others of $R^{22}$, $R^{23}$, $R^{24}$ and $R^{25}$ are hydrogen, can be prepared by reacting a compound of formula XX

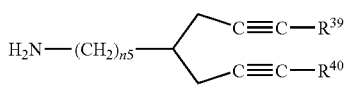

XX where $n^5$ is as hereinbefore defined and $R^{39}$ and $R^{40}$ are each independently hydrogen or $C_1$-$C_{10}$-alkyl, with a compound of formula XXI

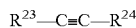   XXI where at least one of $R^{23}$ and $R^{24}$ is a 5- to 12-membered heterocyclic ring wherein at least one of the ring atoms is nitrogen, oxygen or sulphur, that ring being optionally substituted by halo, cyano, hydroxy, carboxy, aminocarbonyl, nitro, $C_1$-$C_{10}$-alkyl, $C_1$-$C_{10}$-alkoxy or $C_3$-$C_{10}$-cycloalkyl, and the other is hydrogen.

Compounds of formula IV are novel compounds, which may be prepared by reaction of a compound of formula XXII

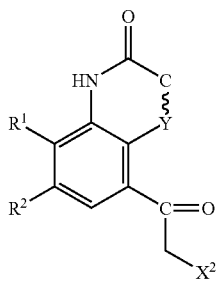

XXII or a protected form thereof where —C~Y—, $R^1$ and $R^2$ are as hereinbefore defined and $X^2$ is a halogen atom, preferably chlorine or bromine, with a compound of formula III as hereinbefore defined. The reaction may be carried out using conventional procedures, for example those described by Yoshizaki et al, *J. Med. Chem.* 1976, 19, 1138, or analogously as hereinafter described in the Examples.

Compounds of formula V are known or may be prepared by reacting a compound of formula II where —C~Y—, $R^1$ and $R^2$ are as hereinbefore defined with ammonia or a protected form thereof or azide using known methods for reacting epoxides with amines or analogously as hereinafter described in the Examples. Where a compound of formula II is reacted with azide a reduction step is subsequently required to yield the compound of formula V.

Compounds of formula VI and VII are known or may be prepared by known procedures such as those described in Liebigs Ann. Chem. 1985, 435.

Compounds of formula VIII are known or may be prepared by methods analogous to those used for the preparation of known compounds, for example those used in the Examples hereinafter.

Compounds of formula IX are known or may be prepared by known procedures.

Compounds of formula X may be prepared as described in international patent application WO 96/23760 or by analogous procedures.

Compounds of formula XI are known or may be prepared by known procedures.

Compounds of formula XII may be prepared as described in international patent application WO 96/23760 or by analogous procedures.

Compounds of formula XIII are known or may be prepared by known procedures.

Compounds of formula XIV may be prepared by reacting a compound of formula XXIII

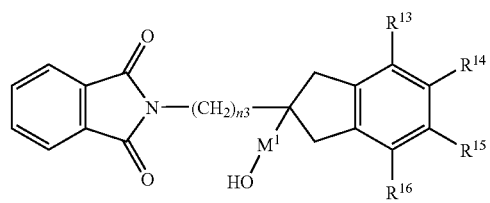

XXIII where $R^{13}$, $R^{14}$, $R^{15}$, $R^{16}$ and $n^3$ are as hereinbefore defined and $M^1$ is $C_1$-$C_{10}$-alkylene, with a compound of formula XXIV

   XXIV or protected form thereof where E is $C_1$-$C_{10}$-alkyl/$C_1$-$C_{10}$-alkylene or $C_7$-$C_{15}$-aralkyl/$C_7$-$C_{15}$-aralkylene and $L^2$ is a leaving atom or group. The reaction may be carried out using known methods for converting hydroxyl groups to alkoxy or aralkyloxy groups. For example a compound of formula XXIII may be conveniently reacted with diazomethane or a diazomethane equivalent such as (trimethylsilyl)diazomethane using the procedure described in *Tet. Lett.* 1990, vol. 31, 5507 to give a compound of formula XIV where $R^{12}$ is $C_1$-$C_8$-alkylene substituted by methoxy. The reaction is conveniently carried out in an organic solvent, for example dichloromethane, preferably in the presence of a strong acid such as fluoroboric acid or analogously as hereinafter described in the Examples. The reaction temperature is conveniently from −10 to 10° C., but preferably about 0° C.

Compounds of formula XV may be prepared by reacting a compound of formula XXV

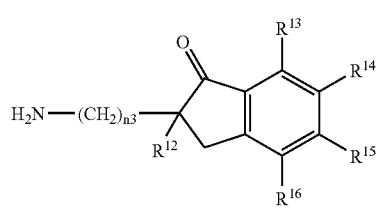

XXV where $R^{12}$, $R^{13}$, $R^{14}$, $R^{15}$, $R^{16}$ and $n^3$ are as hereinbefore defined, with a compound of formula XXVI

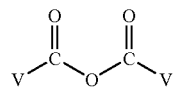

XXVI where each V is a halo-$C_1$-$C_8$-alkyl, especially for example in both cases trifluoromethyl (i.e. giving trifluoroacetic anhydride). The reaction may be carried out using known procedures for reacting primary amines with anhydrides or analogously as hereinafter described in the Examples. The reaction is conveniently carried out in an organic solvent, for example tetrahydrofuran, preferably in the presence of a base such as triethylamine. The reaction temperature is conveniently from 10 to 60° C., but preferably room temperature.

Compounds of formula XVI may be prepared by reacting a compound of formula XXVII

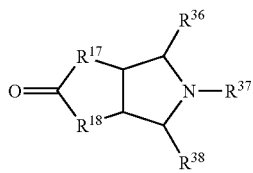

XXVII or a protected form thereof where $R^{17}$, $R^{18}$, $R^{36}$, $R^{37}$ and $R^{38}$ are as hereinbefore defined, with hydroxylamine or preferably a salt thereof. The reaction may be carried out using known procedures for converting ketones to oximes, for example as described by Davis et al in *J. Org. Chem.* 1989, 54, 2021, or analogously as hereinafter described in the Examples. The reaction is conveniently carried out in a solvent, for example a mixture of ethanol and water, preferably in the presence of an inorganic base such as sodium acetate. The reaction temperature is conveniently from 80° C. to reflux temperature.

Compounds of formula XVII may be prepared by converting a compound of formula XXVIII

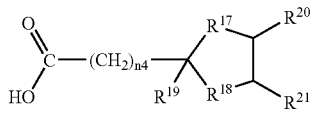

XXVIII or a protected form thereof wherein $R^{17}$, $R^{18}$, $R^{19}$, $R^{20}$, $R^{21}$ and $n^4$ are as hereinbefore defined, to the corresponding acyl-azide, for example by treating with ethyl chloroformate and triethylamine, and then subjecting the acyl azide to thermolysis in an inert solvent such as toluene at a temperature from 50-100° C. The reaction may be carried out using known procedures for converting carboxylic acids to isocyanates, for example by way of a Curtius rearrangement as described in *J. Org. Chem.* 1962, 27, 4465, or analogously as hereinafter described in the Examples.

Compounds of formula XVIII may be prepared as described in international patent application WO 96/23760 or by analogous procedures.

Compounds of formula XIX are known or may be prepared by known procedures.

Compounds of formula XX may be prepared as described in international patent application WO 96/23760 or by analogous procedures.

Compounds of formula XXI are known or may be prepared by known procedures.

Compounds of formula XXII are known or may be prepared by known procedures, for example those disclosed in United States patent specification U.S. Pat. No. 4,460,581 and German patent specification DE 3134590.

Compounds of formula XXIII may be prepared by reacting a compound of formula XXIX

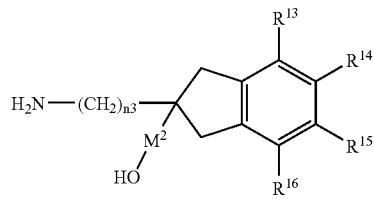

XXIX where $R^{13}$, $R^{14}$, $R^{15}$, $R^{16}$ and $n^3$ are as hereinbefore defined and $M^2$ is $C_1$-$C_{10}$-alkylene, with phthalic anhydride. The reaction may be carried out using known procedures for reacting amines with phthalic anhydride or analogously as hereinafter described in the Examples. The reaction can be carried out in an organic solvent but it is preferably carried out using neat phthalic anhydride. The reaction temperature is conveniently from 120 to 200° C., but preferably about 200° C.

Compounds of formula XXIV are known or may be prepared by known procedures.

Compounds of formula XXV are known or may be prepared by aminating a compound of formula XXX

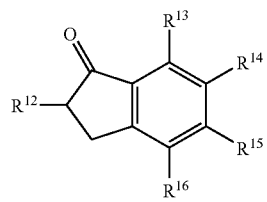

XXX where $R^{12}$, $R^{13}$, $R^{14}$, $R^{15}$ and $R^{16}$ are as hereinbefore defined, for example using ammonia and potassium hexacyanoferrate $K_3Fe(CN)_6$ in the procedure described in Farnum and Carlson, *Synthesis* 1972, 191, or analogously as hereinafter described in the Examples. The reaction temperature is conveniently from 60 to 100° C., but preferably about 80° C.

Compounds of formula XXVI are known or may be prepared by known procedures.

Compounds of formula XXVII may be prepared by reacting a compound of formula XXXI

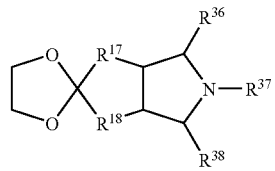

XXXI or a protected form thereof where $R^{17}$, $R^{18}$, $R^{36}$, $R^{37}$ and $R^{38}$ are as hereinbefore defined, with an aqueous acid, for example hydrochloric acid. The reaction may be carried out using known procedures for converting dioxolanes to ketones, or analogously as hereinafter described in the Examples. The reaction is conveniently carried out in an organic inert solvent, for example acetone. The reaction temperature is conveniently from ambient to reflux temperature.

Compounds of formula XXVIII may be prepared by the procedure described in international patent application WO 99/02517, or analogously as hereinafter described in the Examples. When $n^4$ is 0 those compounds may be prepared from the corresponding bis(halo-alkyl) substituted heterocycle, such as those disclosed in *Org. Process Res. Dev.* 2002, 6, 938, using the procedure that is also described in international patent application WO 99/02517, or analogously as hereinafter described in the Examples.

Compounds of formula XXIX are known or may be prepared by reducing a compound of formula XXXII

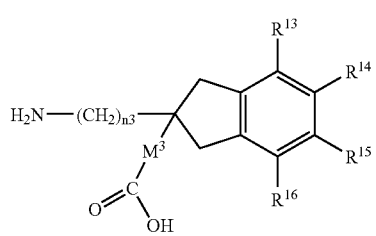

XXXII where $R^{13}$, $R^{14}$, $R^{15}$ and $R^{16}$ are as hereinbefore defined and $M^3$ is $C_1$-$C_9$-alkylene or a bond. The reaction may be carried out using known procedures for reducing carboxylic acids to give primary alcohols, for example using lithium aluminium hydride in ether as described in "Advanced Organic Chemistry", J. March, Wiley, 4$^{th}$ edition 1992, page 1212, or analogously as hereinafter described in the Examples. The reaction temperature is conveniently from 10 to 40° C., but preferably room temperature.

Compounds of formula XXX are known or may be prepared by known procedures, for example the procedure described in *J. Mol. Catal. A.* 2000, 154, 237, or analogously as hereinafter described in the Examples.

Compounds of formula XXXI may be prepared by reacting a compound of formula XXXIII

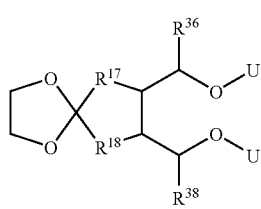

XXXIII or a protected form thereof where $R^{17}$, $R^{18}$, $R^{36}$ and $R^{38}$ are as hereinbefore defined and U is a $C_1$-$C_8$-alkyl when $R^{36}$ and $R^{38}$ are both oxo or U is a $C_1$-$C_8$-alkyl-sulfonyl group when $R^{36}$ and $R^{38}$ are both other than oxo, with a compound of formula XXXIV

 XXXIV where $R^{37}$ is as hereinbefore defined. The reaction may be carried out using known procedures for reacting carboxylic esters or sulfonic esters with amines, for example [Ex. 81] when U is a $C_1$-$C_8$-alkyl that described by Gais et al in *J. Org. Chem.* 1989, 54, 5115, or [Ex. 85] when U is an $C_1$-$C_8$-alkyl-sulfonyl group that described by Guzikowski et al in *J. Med. Chein.* 2000, 43, 984, or analogously as hereinafter described in the Examples. The reaction is conveniently carried out in an organic inert solvent, for example acetone. The reaction temperature is conveniently from ambient to reflux temperature.

Compounds of formula XXXII are known or may be prepared by known procedures, for example the procedure described in *J. Med. Chem.* 1991, 34, 3125, or analogously as hereinafter described in the Examples.

Compounds of formula XXXIII are known or may be prepared by known procedures, for example when U is a $C_1$-$C_8$-alkyl that described by Gais et al in *J. Org. Chem.* 1989, 54, 5115, or analogously as hereinafter described in the Examples. When U is a $C_1$-$C_8$-alkyl-sulfonyl group those compounds can be prepared by reacting the corresponding alcohol, such as those disclosed in *Tet. Lett.* 2002, 43, 4947, with the relevant alkyl-sulfonyl halide, for example using the procedure disclosed in "March's Advanced Organic Chemistry: Reactions, Mechanisms, and Structure", M. B. Smith and J. March, Fifth Edition, 2001, page 587 or analogously as hereinafter described in the Examples.

Compounds of formula XXXIV are known or may be prepared by known procedures.

Where desired, the protection of any reactive group may be carried out at any appropriate stage in the above processes. The protecting group is suitably one used conventionally in the art such as preferably benzyl or trifluoroacetyl and may be introduced and removed using a conventional procedure, for example using an amine-protective group as described in Protective Groups in Organic Synthesis, T. W. Greene, P. G. M. Wuts, John Wiley & Sons Inc, Third Edition, 1999. When a hydroxy group is protected by a benzyl group, the latter may be removed by catalytic hydrogenation in the presence of palladium on charcoal using conventional procedures, such as those used hereinafter in the Examples.

Compounds of formula I in free, salt or solvate form are useful as pharmaceuticals. Accordingly the invention also provides a compound of formula I in free, salt or solvate form for use as a pharmaceutical. The compounds of formula I in free, salt or solvate form, hereinafter referred to alternatively as "agents of the invention", have good $\beta_2$-adreno-receptor agonist activity. The $\beta_2$ agonist activity, onset of action and duration of action of the agents of the invention may be tested using the guinea pig tracheal strip in vitro assay according to the procedure of R. A. Coleman and A. T. Nials, *J. Pharmacol. Methods* 1989, 21, 71. The binding potency and selectivity for the $\beta_2$-adrenoreceptor relative to the $\beta$1-adrenoreceptor can be measured by a classical filtration binding assay according to the procedure of Current Protocols in Pharmacology (S. J. Enna (editor-in-chief) et at, John Wiley & Son, Inc, 1998), or by cAMP determination in cells expressing $\beta_2$- or $\beta_1$-adrenoceptor, according to the procedure of B. January et at, *Brit. J. Pharmacol.* 1998, 123, 701.

The agents of the invention commonly have a rapid onset of action and have a prolonged stimulating action on the $\beta_2$-adrenoreceptor, compounds of the Examples hereinbelow having $K_i$ ($\beta_2$) values of the order of 0.1 to 1000 nM, having durations of action of the order of 1 to greater than 12 hours. Many of the compounds have binding selectivites for the 2-adrenoreceptor relative to the $\beta_1$-adrenoreceptor from 1.5 to 500.

The compounds of Examples 1, 3, 4, 30, 33, 35, 55, 85 and 139 have $\beta_2$ and $\beta_1$ binding potencies, measured by a classical filtration binding assay, represented by $K_i$ values ($\beta_2/\beta_1$) (in µM) of 0.026/0.186, 0.054/0.050, 0.006/0.115, 0.077/0.132, 0.048/0.491, 0.0004/0.006, 0.1278/0.3835, 0.121/0.380 and 0.003/0.004 respectively.

Having regard to their $\beta_2$ agonist activity, the agents of the invention are suitable for use in the treatment of any condition which is prevented or alleviated by activation of the $\beta_2$-adrenoreceptor. In view of their long acting selective $\beta_2$ agonist activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.*, 1997, 156, 766 and analogous models. The agents of the invention are therefore useful in the treatment of obstructive or inflammatory airways diseases. In view of their long duration of action, in most cases it is possible to administer the agents of the invention once-a-day in the treatment of such diseases. In another aspect, agents of the invention commonly exhibit characteristics indicating a low incidence of side effects commonly encountered with $\beta_2$ agonists such as tachycardia, tremor and restlessness, such agents accordingly being suitable for use in on demand (rescue) treatment as well as prophylactic treatment of obstructive or inflammatory airways diseases.

Treatment of a disease in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their $\beta_2$ agonist activity, the agents of the invention are also useful in the treatment of a condition requiring relaxation of smooth muscle of the uterus or vascular system. They are thus useful for the prevention or alleviation of premature labour pains in pregnancy. They are also useful in the treatment of chronic and acute urticaria, psoriasis, allergic conjunctivitis, actinitis, hay fever, and mastocytosis.

The agents of the invention are also useful as co-therapeutic agents for use in combination with other drug substances such as anti-inflammatory, bronchodilatory, antihistamine, immunosuppressive or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such as those described in U.S. Pat. No. 5,451,700; LTD4 antagonists such as montelukast and zafirlukast; PDE4 inhibitors such as cilomilast (Ariflo® GlaxoSmithKline), Roflumilast (Byk Gulden),V-11294A (Napp), BAY19-8004 (Bayer), SCH—351591 (Schering-Plough), Arofylline (Almirall Prodesfarma), PD189659 (Parke-Davis), AWD-12-281 (Asta Medica), CDC-801 (Celgene), SelCID(TW) CC-10004 (Celgene), KW-4490 (Kyowa Hakko Kogyo), WO 03/104204, WO 03/104205, WO 04/000814, WO 04/000839 and WO 04005258 (Merck), as well as those described in WO 98/18796 and WO 03/39544; A2a agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; A2b antagonists such as those described in WO 02/42298;

Such bronchodilatory drugs include anticholinergic or antimuscarinic agents, in particular ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/53966, EP 424021, U.S. Pat. No. 5,171, 744, U.S. Pat. No. 3,714,357 and WO 03/33495.

The agents of the invention are also useful as co-therapeutic agents for use in combination other beta-2 adrenoceptor agonists, for example as a rescue medication. Suitable beta-2 adrenoceptor agonists include albuterol (salbutamol), metaproterenol, terbutaline, salmeterol, fenoterol, procaterol, and especially, formoterol and pharmaceutically acceptable salts thereof, and compounds (in free or salt or solvate form) of formula I of WO 00/75114, which document is incorporated herein by reference, preferably compounds of the Examples thereof, especially a compound of formula

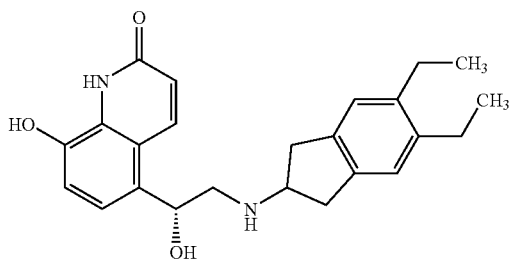

and pharmaceutically acceptable salts thereof, as well as compounds (in free or salt or solvate form) of formula I of WO 04/16601.

Co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, PDE4 inhibitors, A2a agonists, A2b agonists or LTD4 antagonists may be used, for example, in the treatment of COPD or, particularly, asthma. Combinations of agents of the invention and anticholinergic or antimuscarinic agents, PDE4 inhibitors, A2a agonists, A2b agonists, dopamine receptor agonists or LTB4 antagonists may be used, for example, in the treatment of asthma or, particularly, COPD.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages employed in practising the invention will of course vary depending, for example, on the particular condition to be treated, the effect desired and the mode of administration. In general, suitable daily dosages for administration by inhalation are of the order of from 1 to 5000 µg.

The invention is illustrated by the following Examples.

EXAMPLES

Especially preferred compounds of formula I include compounds of formula XXXV

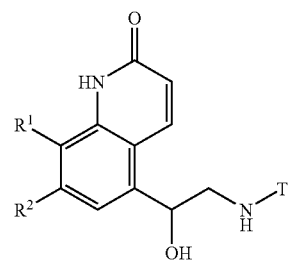

XXXV wherein $R^1$, and $R^2$ and T are as shown in the following table, the method of preparation being described hereinafter. All compounds are in the free form. 1H NMR spectra are recorded at 400 MHz in CDCl$_3$ unless otherwise noted. Mass spectra are obtained under electrospray ionisation conditions with LC gradient elution of 5% to 95% acetonitrile-water in the presence of 0.1% formic acid.

TABLE 1

| Ex | $R^1$ | $R^2$ | T | MH+ |
|---|---|---|---|---|
| 1 | —OH | —H | | 337 |

TABLE 1-continued

| Ex | R¹ | R² | T | MH+ |
|---|---|---|---|---|
| 2 | —OH | —H | (1-methyl-indanyl) | 337 |
| 3 | —OH | —H | (5-butyl-1-methyl-indanyl) | 393 |
| 4 | —OH | —H | (1,2-dimethyl-indanyl) | 351 |
| 5 | —OH | —H | (1-methyl-tetralinyl) | 351 |
| 6 | —OH | —H | (1,2,3-trimethyl-indanyl) | 362 |
| 7 | —OH | —H | (2-ethyl-indanyl) | 351 |
| 8 | —OH | —H | (1-ethyl-1-benzyl-indanyl) | — |
| 9 | —OH | —H | (2-ethyl-2-methoxymethyl-indanyl) | — |
| 10 | —OH | —H | (2-ethyl-2-methoxy-5,6-diethyl-indanyl) | — |
| 11 | —OH | —H | (4-methyl-thiochromanyl) | — |
| 12 | —OH | —H | (5-ethyl-1-methyl-indanyl) | — |
| 13 | —OH | —H | (5-propyl-1-methyl-indanyl) | — |
| 14 | —OH | —H | (2-ethyl-5,6-dimethyl-indanyl) | — |
| 15 | —OH | —H | (3-methyl-6-ethyl-chromanyl) | — |
| 16 | —OH | —H | (3-methyl-7-ethyl-chromanyl) | — |
| 17 | —OH | —H | (3-methyl-7-methyl-chromanyl) | — |
| 18 | —OH | —H | (1-methyl-6-methoxy-tetralinyl) | — |
| 19 | —OH | —H | (4-methyl-8-ethyl-isochromanyl) | — |
| 20 | —OH | —H | (1,2-dimethyl-6-methyl-tetralinyl) | — |
| 21 | —OH | —H | (spiro bis-indanyl) | 426 |

TABLE 1-continued

| Ex | R¹ | R² | T | MH+ |
|----|----|----|---|-----|
| 22 | —OH | —H | 2-(thiophen-2-yl)-1-methyl-indan-1-ol structure | — |
| 23 | —OH | —H | 5,6-dimethyl-indan structure with CH₃ and OH | — |
| 24 | —OH | —H | 1,5,6-trimethyl-indan structure | — |
| 25 | —OH | —H | 5,6-bis(CH₂CH₃)-indan structure | — |
| 26 | —OH | —H | 1,1-dimethyl-5,6-bis(CH₂CH₃)-indan structure | — |
| 27 | —OH | —H | 1,1,2-trimethyl-5,6-bis(CH₂CH₃)-indan structure | — |
| 28 | —OH | —H | 1-methoxy-5,6-bis(CH₂CH₃)-indan structure | — |

Preparation of Starting Materials

2,2',4-Trimethoxybenzophenone oxime

Hydroxylamine hydrochloride (4.98 g, 71.7 mmol) is added to a solution of 2,2',4-tri-methoxybenzophenone (*J. Org. Chem.* 1996, 61, 6326; 6.5 g, 23.9 mmol) in ethanol (50 ml) and pyridine (10 ml). The mixture is heated at reflux for 2 hours and the solvent evaporated. The residue is partitioned between dichloromethane and 2 M aqueous HCl and the organic phase is washed with water, brine, dried (MgSO₄) and evaporated to afford the title compound.

C-(2,4-Dimethoxyphenyl)-C-(2-methoxyphenyl) methylamine 2,2',4-Trimethoxybenzophenone oxime (6 g, 20.9 mmol) is dissolved in ethanol (30 ml) and concentrated aqueous ammonia (150 ml). Ammonium acetate (0.81 g, 10.45 mmol) is added, followed by zinc powder (6.79 g, 104 mmol). The reaction is heated to reflux for 4 hours, cooled to ambient temperature, diluted with ethyl acetate and filtered through a Celite™ filter. Evaporation affords the title compound. $\delta_H$ 3.78 (s 3H), 3.80 (s 3H), 3.82 (s 3H), 5.62 (s 3H), 6.40-6.50 (m 2H), 6.85-9.95 (m 2H), 7.10 (d J 8), 7.20-7.30 (m 2H)

8-Benzyloxy-5-(R-2-{[(2,4-dimethoxyphenyl)-(2-methoxyphenyl)methyl]amino}-1-hydroxyethyl)-1H-quinolin-2-one A mixture of C-(2,4-dimethoxyphenyl)-C-(2-methoxyphenyl)methylamine (0.934 g, 3.42 mmol) and R-8-benzyloxy-5-oxiranyl-1H-quinolin-2-one (0.50 g, 1.71 mmol) in CHCl₃ (2 ml) is heated at 110° C. and the solvent allowed to evaporate. The residue is heated for 16 hours to afford the title compound, MH+567

5-(R-2-Amino-1-hydroxyethyl)-8-benzyloxy-1H-quinolin-2-one

A solution of 8-benzyloxy-5-(R-2-{[(2,4-dimethoxyphenyl)-(2-methoxyphenyl)methyl]-amino}-1-hydroxyethyl)-1H-quinolin-2-one (0.70 g, 1.24 mmol) in acetic acid (10 ml) and water (10 ml) is heated at 80° C. for 4 hours. The solvent is evaporated and the crude product purified by reverse phase flash chromatography, eluting with 0% to 50% acetonitrile-water gradient to afford the title compound. $\delta_H$ 2.65 (m 1H), 2.95 (m 1H), 3.70-3.80 (m 11H), 5.10 (m 1H), 5.15 (s 1H), 5.55 (m 1H), 6.40-7.40 (m 16H), 7.9 (m 1H), 9.10 (br s 1H).

1-(4-n-Butlphenyl)-3-chloropropan-1-one

A mixture of 3-chloropropionyl chloride (8.59 ml, 89.9 mmol) and n-butylbenzene (14.02 ml, 89.9 mol) is added dropwise to a cooled (0° C.) solution of aluminium chloride (26.93 g, 202 mmol) in nitromethane (54 ml). The mixture is allowed to warm to ambient temperature for 4 hrs, then poured into a mixture of ice and concentrated hydrochloric acid. The layers are separated and the aqueous phase is extracted with ether. The combined organic phases are washed with brine, dried (MgSO₄) and evaporated to afford the title compound, NMR $\delta_H$ 0.85 (t J 7.3 3H), 1.25 (sextet J 7.3 2H), 1.55 (quintet J 7.3 2H), 3.34 (t J 6.9 2H), 3.84 (t J 6.9 2H), 7.20 (d J 8.3 2H), 7.80 (d J 8.3 2H)

5-n-Butylindan-1-one

A solution of 1-(4-n-butylphenyl)-3-chloropropan-1-one (17.88 g, 79.8 mmol) in concentrated sulphuric acid (69 ml) is heated at 90° C. for 4 hours. After cooling to ambient temperature, the reaction mixture is poured on to ice and extracted with toluene. The combined organic phases are washed with saturated NaHCO₃, brine, dried (MgSO₄) and evaporated to afford the title compound. NMR $\delta_H$ 0.85 (t J 7.3 3H), 1.28 (sextet J 7.3 2H), 1.56 (quintet J 7.3 2H), 2.6 (m 4H), 3.02 (t J 5 2H), 7.10 (d J 8.3 1H), 7.20 (s 11H), 7.60 (d J 8.3 2H)

5-n-Butylindan-1-one oxime

Hydroxylamine hydrochloride (0.89 g, 12.8 mmol) and sodium acetate (12.8 mmol) are added to a solution of 5-n- butylindan-1-one (1.0 g, 5.31 mmol) in ethanol (30 ml) and water (3 ml). The reaction is heated to reflux for 20 minutes, then water is added and the mixture is extracted with $CH_2Cl_2$. The combined organic extracts are washed with brine, dried ($MgSO_4$) and evaporated to afford the title compound. NMR $\delta_H$ 0.86 (t J 7.3 3H), 1.28 (sextet J 7.3 2H), 1.52 (quintet J 7.3 2H), 2.55 (t J 8.0 2H), 2.85-3.0 (m 4H), 7.0 (d J 8.3 1H), 7.05 (s 1H), 7.45 (d J 8.3 2H)

5-n-Butylindan-1-ylamine

A suspension of 5-n-butylindan-1-one oxime (0.50 g, 2.46 mmol) and 10% Pd/C (0.50 g) in acetic acid (50 ml) is hydrogenated at 3.5 bar for 16 hours. The reaction is filtered through a Celite™ filter pad and partitioned between ether and water. The organic phase is washed with saturated $NaHCO_3$ then brine and dried ($MgSO_4$). Evaporation affords the title compound. NMR $\delta_H$ 0.85 (t J 7.3 3H), 1.26 (sextet J 7.3 2H), 1.50 (quintet J 7.3 2H), 1.58 (m 1H), 2.10 (br s 1H), 2.40 (m 1H), 2.50 (t J 8.0 2H), 2.70 (m 1H), 2.88 (m 1H), 4.38 (t J 6 1H), 6.95 (m 3H), 7.16 (d J 8.3 2H)

Methyl 3-phenylbutyrate

Thionyl chloride (44 ml, 91.4 mmol) is added dropwise to methanol (30 ml) at 0° C., followed by 3-phenylbutyric acid (10 g, 60.9 mmol). The reaction is stirred for 4 hours and the solvent is evaporated. The residue is partitioned between t-butylnethyl ether and aqueous ammonia. The organic phase is washed with water and brine, dried ($Na_2SO_4$) and evaporated to afford the title compound. MH+179.

Methyl 2-acetyl-3-phenylbutyrate n-Butyllithium (2.5 M hexanes 12.4 ml, 30.9 mmol) is added to N,N-diisopropylamine (4.4 ml, 31.4 mmol) in tetrahydrofuran (THF, 50 ml) at 0° C. After 10 minutes, the resultant solution is transferred via cannula to a cooled (−78° C.) solution of methyl 3-phenylbutyrate (5.0 g, 28.05 mmol) in THF (50 ml). After 40 minutes, the resultant solution is transferred via cannula to a solution of acetyl chloride (19.15 ml) in THF (50 ml). The resultant mixture is stirred at −78° C. for 1.5 hours, then warmed to 0° C. after which water is added and the mixture is then poured into saturated $NaHCO_3$ and extracted with EtOAc. The combined organic phases are washed with brine, dried ($MgSO_4$) and evaporated. Purification by flash chromatography (12:1 EtOAc-hexane elution) affords the title compound. $\delta_H$ 1.3 (d J 7 3H), 2.3 (s 3H), 3.4 (s 3H), 3.6 (m 1H), 3.8 (m 1H), 7.2-7.4 (m 5H)

1,3-Dimethyl-1H-indene-2-carboxylic acid

Concentrated sulphuric acid (15 ml) is added to methyl 2-acetyl-3-phenylbutyrate (2.75 g, 12.5 mmol) maintaining the temperature below 30° C. The reaction is stirred at ambient temperature for 5 hours, poured on to ice and extracted with EtOAc. The combined organic extracts are evaporated and the residue is diluted with water and the pH adjusted to 8 with saturated $NaHCO_3$. After washing with EtOAc, the aqueous phase is acidified with concentrated HCl and extracted with EtOAc. The combined organic phases are washed with brine, dried ($MgSO_4$) and evaporated to afford the title compound, MH+189.

(1S,2S,3R)-1,3-Dimethylindan-2-carboylic acid

A suspension of 1,3-dimethyl-1H-indene-2-carboxylic acid (0.362 g, 1.92 mmol) and 10% palladium on carbon (110 mg) in acetic acid (20 ml) is hydrogenated at 0.35 bar for 23 hours. The reaction mixture is filtered and the filtrate evaporated to afford the title compound. $\delta_H$ (DMSO-d6) 1.4 (d J 6 6G, 3.35 (t J 6 1H), 3.45 (quintet J 6 2H), 7.1-7.3 (m 4H), 10-11 (br s 1H)

(1S,2R,3R)-1,3-Dimethylindan-2-ylamine

Ethyl chloroformate (0.18 ml, 1.88 mmol) is added to a cooled (0° C.) solution of (1S,2S,3R)-1,3-dimethylindan-2-carboxylic acid (0.298 g, 1.57 mmol) and triethylamine (0.263 ml, 1.88 mmol) in acetone (3 ml) and water (0.5 ml). After 30 minutes, a solution of sodium azide (0.153 g, 2.36 mmol) in water (1 ml) is added and the reaction is stirred at 5° C. for 1 hour, prior to addition of brine and ice. The mixture is extracted with ether and the combined extracts are dried ($Na_2SO_4$) and evaporated. The resultant acyl azide is taken into toluene (6 ml) and heated at 100° C. until nitrogen evolution ceases After evaporation of solvent, the resultant isocyanate is taken into 6N HCl (2.5 ml) and heated at 100° C. for 16 hours. The reaction mixture is evaporated, basified with saturated $NaHCO_3$ and extracted with ethyl acetate. The combined organic extracts are washed with brine, dried ($Na_2SO_4$) and evaporated to afford the title compound. MH+162.

Indan-2-ylmethylamine

Ethyl chloroformate (3.3 ml, 34 mmol) is added to a cooled (0° C.) solution of indan-2-yl acetic acid (5.0 g, 28.4 mmol) and triethylamine (4.75 ml, 34 mmol) in acetone (40 ml) and water (8 ml). After 30 minutes, a solution of sodium azide (2.8 g, 42.6 mmol) in water (16 ml) is added and the reaction is stirred at 5° C. for 1 hour, prior to addition of brine and ice. The mixture is extracted with ether and the combined extracts are dried ($Na_2SO_4$) and evaporated. The resultant acyl azide is taken into toluene (50 ml) and heated at 100° C. until nitrogen evolution ceases. After evaporation of solvent, the resultant isocyanate is taken into 6N HCl (40 ml) and heated at 100° C. for 16 hours. The reaction mixture is evaporated to ⅓ volume and the resultant solid collected by filtration, washed with water and ether, then dried. The resultant hydrochloride salt is suspended in ether (20 ml) and ammonia is bubbled for 10 minutes. Water is added and the organic layer is separated, dried ($Na_2SO_4$) and evaporated to afford the title compound [MH+$CH_3CN$]+189.

Preparation of Final Compounds

Example 1

8-Hydroxy-5-[R-1-hydroxy-2-(R-indan-1-ylamino) ethyl]-1H-quinolin-2-one

N,O bis-(trimethylsilyl)acetamide (93 μl, 0.37 mmol) is added to a solution of R-1-aminoindane (96.3 μl, 0.75 mmol) in DMF (0.6 ml) and the mixture stirred at ambient temperature for 30 minutes. A solution of R-8-benzyloxy-5-oxiranyl-1H-quinolin-2-one (0.147 g, 0.50 mmol) in DMF (0.9 ml) is added and the mixture heated at 80° C. for 36 hours. The reaction mixture is added to water and extracted with ether-EtOAc (1:1); the organic phase is evaporated and purified by flash column chromatography (EtOAc elution) to afford 8-benzyloxy-5-[R-1-hydroxy-2-(R-indan-1-ylamino)ethyl]-1H quinolin-2-one, MH+427.

A suspension of 8-benzyloxy-5-[R-1-hydroxy-2-(R-indan-1-ylamino)ethyl]-1H quinolin-2-one (35 mg, 0.08 mmol) and 10% Pd/C (15 mg) in ethanol (11 ml) is hydrogenated at 0.35 bar for 1 hour. The reaction mixture is filtered through a Celite™ filter plug, washed with ethanol and the combined filtrate and washings are evaporated. The crude product is purified by flash column chromatography (10:1 $CH_2Cl_2$-MeOH elution) to afford 8-hydroxy-5-[R-1-hydroxy-2-(R-indan-1-ylamino)ethyl]-1H-quinolin-2-one, MH+337.

Example 2

8-Hydroxy-5-[R-1-hydroxy-2-(S-indan-1-ylamino)ethyl]-1H-quinolin-2-one

This is prepared using a method analogous to Example 1, MAH+427 but using S-1-aminoindane as the starting material.

Example 3

5-[R-2-(RS-5-butylindan-1-ylamino)-1-hydroxyethyl]-8-hydroxy-1H-quinolin-2-one

This compound is prepared using procedures analogous to those used in Example 1, using R-8-benzyloxy-5-oxiranyl-1H-quinolin-2-one and 5-n-butylindan-1-ylamine, MH+393

Example 4

8-Hydroxy-5-[R-1-hydroxy-2-(1R,2S-1-methylindan-2-ylamino)ethyl]-1H-quinolin-2-one and 8-hydroxy-5-[R-1-hydroxy-2-(1S,2R-1-methylindan-2-ylamino)ethyl]-1H-quinolin-2-one A mixture of (±) cis-1-methylindan-2-yl amine (*J. Chein. Soc.* (C), 1970, 920), (0.351 g, 2.38 mmol) and R-8-benzyloxy-5-oxiranyl-1H-quinolin-2-one (0.350 g, 1.19 mmol) in 2-methoxyethyl ether (2 ml) is heated in a sealed tube at 190° C. for 16 hours. The solvent is evaporated and the crude product purified by flash column chromatography (20:1 $CH_2Cl_2$-MeOH elution) to afford a 1:1 mixture of 8-benzyloxy-5-[R-1-hydroxy-2-(1R,2S-1-methylindan-2-ylamino)ethyl]-1H-quinolin-2-one and 8-benzyloxy-5-[R-1-hydroxy-2-(1S,2R-1-methylindan-2-ylamino)ethyl]-1H-quinolin-2-one, MU+441. A suspension of 8-benzyl-oxy-5-[R-1-hydroxy-2-(1R,2S-1-methylindan-2-ylamino)ethyl]-1H-quinolin-2-one and 8-benzyloxy-5-[R-1-hydroxy-2-(1S,2R-1-methylindan-2-ylamino)ethyl]-1H-quinolin-2-one (0.100 g, 0.23 mmol) and 10% Pd/C (10 mg) in ethanol (8 ml) is hydrogenated at 0.35 bar for 2 hours. The reaction is filtered through a Celite™ filter plug and washed with ethanol. The combined filtrate and washings are evaporated to afford a 1:1 mixture of 8-hydroxy-5-[R-1-hydroxy-2-(1R,2S-1-methylindan-2-ylamino)ethyl]-1H-quinolin-2-one and 8-hydroxy-5-[R-1-hydroxy-2-(1S,2R-1-methylindan-2-ylamino)ethyl]-1H-quinolin-2-one, MH+351.

Example 5

8-Hydroxy-5-{R-1-hydroxy-2-[R-(1,2,3,4-tetrahydronaphthalen-1-yl)amino]-ethyl}-1H-quinolin-2-one R-1-Amino-1,2,3,4-tetrahydronaphthalene (0.301 g, 2.0 mmol) and R-8-benzyloxy-5-oxiranyl-1H-quinolin-2-one (0.200 g, 0.68 mmol) are heated neat in sealed tube at 110° C. for 16 hours. The crude product is purified by preparative LCMS to afford 8-benzyloxy-5-{R-1-hydroxy-2-[R-(1,2,3,4-tetrahydronaphthalen-1-yl)amino]-ethyl}-1H-quinolin-2-one, MH+441. A suspension of 8-benzyloxy-5-{R-1-hydroxy-2-[R-(1,2,3,4-tetrahydronaphthalen-1-yl)amino]-ethyl}-1H-quinolin-2-one (0.155 g, 0.35 mmol) and 10% Pd/C (30 mg) in methanol-trifluoroacetic acid (20:1, 21 ml) is hydrogenated at 0.35 bar for 4 hours. The catalyst is filtered through a Celite™ filter plug and washed with methanol. Evaporation affords 8-hydroxy-5-{R-1-hydroxy-2-[R-(1,2,3,4-tetrahydronaphthalen-1-yl)amino]-ethyl}-1H-quinolin-2-one, MH+351.

Example 6

5-[R-2-(1S,2R,3R-1,3-Dimethylindan-2-ylamino)-1-hydroxyethyl]-8-hydroxy-1H-quinolin-2-one This compound is prepared using procedures analogous to those used in Example 4, but converting (1S,2R,3R)-1,3-dimethylindan-2-ylamine to 8-benzyloxy 5-[R-2-(1S,2R,3R-1,3-dimethylindan-2-ylamino)-1-hydroxyethyl]-1H-quinolin-2-one (MH+455) and deprotecting that compound to give the title compound (MH+365).

Example 7

8-Hydroxy-5-{R-1-hydroxy-2-[(indan-2-ylmethyl)amino]ethyl}-1H-quinolin-2-one

This compound is prepared using procedures analogous to those used in Example 1, but converting indan-2-ylmethylamine to 8-benzyloxy-5-(R-1-hydroxy-2-[(indan-2-ylmethyl)-amino]ethyl)-1H-quinolin-2-one (MH+441) and then deprotecting that compound to give the title compound (MH+351).

Examples 8 to 20

These compounds are prepared using procedures analogous to those used in Example 3, using R-8-benzyloxy-5-oxiranyl-1H-quinolin-2-one and the appropriate amine.

Example 21

5-[R-2-(4b,10-Dihydro-9H-indeno[1,2-a]inden-9a-ylamino) 1-hydroxyethyl]-8-hydroxy-1H-quinolin-2-one $K_3Fe(CN)_6$ (18.0 g, 54.8 mmol) is added to hot (80° C.) degassed water (150 ml), followed by 2-benzylindan-1-one (*J Mol Catal A* 2000, 154, 237; 3.8 g, 17.1 mmol). Concentrated aqueous ammonia (14 ml) is then added over 15 minutes and the reaction mixture is heated at 80-90° C. in the dark for 24 hours. After cooling to ambient temperature, the mixture is extracted with chloroform. The combined chloroform extracts are extracted with 3 M HCl and the acidic extracts are evaporated to afford 2-amino-2-benzylindan-1-one hydrochloride salt, MH+238. A suspension of 2-amino-2-benzylindan-1-one (0.506 g, 2.13 mmol) and 10% Pd/C (0.130 g) in acetic acid (15 ml) is hydrogenated at 0.35 bar for 24 hours. Concentrated sulphuric acid (1.5 ml) is added and the reaction is hydrogenated for a further 7 hours. The catalyst is filtered through a Celite™ filter plug and mixture concentrated in vacuo. The residue is basified to pH 8 with saturated aqueous sodium bicarbonate and extracted with ether. The ether extracts are washed with brine, dried ($Na_2SO_4$) and evaporated. The crude product is purified by flash chromatography (30:1 $CH_2Cl_2$-MeOH elution) to afford 4b,10-dihydro-9H-indeno[1,2-a]inden-9a-ylamine, MH+222. A mixture of 4b,10-dihydro-9H-indeno[1,2-a]inden-9a-ylamine (0.296 g, 1.34 mmol) and R-8-benzyloxy-5-oxiranyl-1H-quinolin-2-one (0.262 g, 0.893 mmol) in 2-methoxyethyl ether (4.5 ml) is heated in a sealed tube at 190° C. for 50 hours. The solvent is evaporated and the crude product purified by preparative LCMS to afford 5-[R-2-(4b,10-dihydro-9H-indeno-[1,2-a]inden-9a-ylamino) 1-hydroxyethyl]-8-benzyloxy-1H-quinolin-2-one, MH+515. A suspension of 5-[R-2-(4b,10-dihydro-9H-indeno[1,2-a]inden-9a-ylamino) 1-hydroxy-ethyl]-8-benzyloxy-1H-quinolin-2-one (10 mg, 0.02 mmol) and 10% Pd/C (8 mg) in ethanol (5 ml) is hydrogenated at 0.35 bar for 30 minutes. The catalyst is filtered through a Celite™ filter plug and the solvent evaporated to afford 5-[R-2-(4b,10-dihydro-9H-indeno[1,2-a]inden-9a-ylamino) 1-hydroxy-ethyl]-8-hydroxy-1H-quinolin-2-one, MH+426.

Examples 22 to 28

These compounds are prepared using procedures analogous to those used in Example 4, using R-8-benzyloxy-5-oxiranyl-1H-quinolin-2-one and the appropriate amine.

Especially preferred compounds of formula I include compounds of formula XXXV as hereinbefore defined wherein $R^1$, $R^2$ and T are as shown in Table 2 below, the method of preparation being described hereinafter. All compounds are in the free form. 1H NMR spectra are recorded at 400 MH in CDCl$_3$ unless otherwise noted. Mass spectra are obtained under electrospray ionisation conditions with LC gradient elution of 5% to 95% acetonitrile-water in the presence of 0.1% formic acid.

TABLE 2

| Ex | $R^1$ | $R^2$ | T | MH+ |
|---|---|---|---|---|
| 29 | —OH | —H | | 339 |
| 30 | —OH | —H | | 395 |
| 31 | —OH | —H | | 305 |
| 32 | —OH | —H | | 287 |
| 33 | —OH | —H | | 371 |
| 34 | —OH | —H | | 357 |
| 35 | —OH | —H | | 393 |
| 36 | —H | —OH | | — |
| 37 | —H | —OH | | — |

TABLE 2-continued
| Ex | R¹ | R² | T | MH+ |
|---|---|---|---|---|
| 38 | —H | —OH | 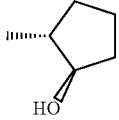 | — |
| 39 | —H | —OH | 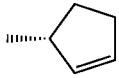 | — |
| 40 | —H | —OH | 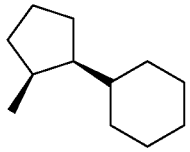 | — |
| 41 | —H | —OH | 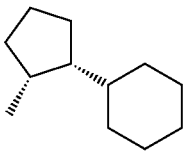 | — |
| 42 | —H | —OH | 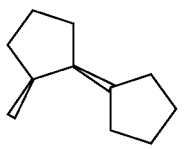 | — |
| 43 | —OH | —H | 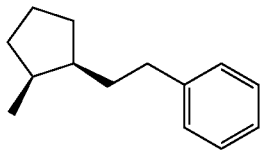 | — |
| 44 | —OH | —H | 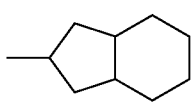 | — |
| 45 | —OH | —H | 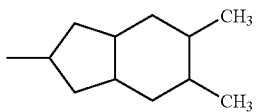 | — |
| 46 | —OH | —H | 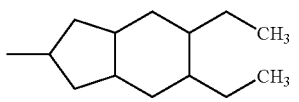 | — |
| 47 | —OH | —H | 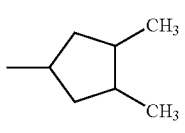 | — |
| 48 | —OH | —H | 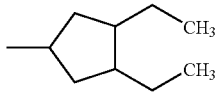 | — |
| 49 | —H | —OH | 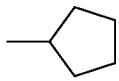 | — |

TABLE 2-continued

| Ex | R¹ | R² | T | MH+ |
|----|----|----|---|-----|
| 50 | —H | —OH | 2,3,3a,4,5,6,7,7a-octahydro-1H-indene with 5,6-dimethyl substituents | — |
| 51 | —H | —OH | 2,3,3a,4,5,6,7,7a-octahydro-1H-indene with 5,6-diethyl substituents | — |
| 52 | —H | —OH | cyclopentyl with 2,3-dimethyl substituents | — |
| 53 | —H | —OH | cyclopentyl with 2,3-diethyl substituents | — |
| 54 | —H | —OH | cyclopentyl | — |

Example 29

8-Hydroxy-5-[R-1-hydroxy-2-(2,3,4,7-tetrahydro-1H-inden-2-ylamino)-ethyl]-1H-quinolin-2-one (a) Liquid ammonia (80 ml) is condensed at −78° C. and 2-aminoindane (2 g, 15 mmol) is added, followed by lithium wire (2 g, 300 mmol) portionwise over 5 minutes. The reaction is stirred at −78° C. for 2 hours, then cautiously quenched with ethanol (100 ml) and warmed to ambient temperature overnight. Water is added, the mixture is extracted with ether and the combined organic extracts are washed with brine, dried (MgSO$_4$) and evaporated to afford 2,3,4,7-tetrahydro-1H-inden-2-ylamine. [M+CH$_3$CN] 177.

(b) N,O-Bis(trimethylsilyl)acetamide (0.464 ml, 1.88 mmol) is added to a solution of 2,3,4,7-tetrahydro-1H-inden-2-ylamine (0.509 g, 3.76 mmol) in N,N-dimethylformamide (DMF) (1 ml) and the mixture stirred at ambient temperature for 30 minutes. 8-Benzyloxy-5-R-oxiranyl-1H-quinolin-2-one (0.736 g, 2.51 mmol) is added and the mixture heated at 80° C. for 4 days. The solvent is evaporated and the crude product purified by flash column chromatography (neat EtOAc-10% methanol-EtOAc gradient elution) to afford 8-benzyloxy-5-[R-1-hydroxy-2-(2,3,4,7-tetrahydro-1H-inden-2-ylamino)ethyl]-1H-quinolin-2-one, MH+443.

(c) 10% Pd/C (20 mg) is added to a solution of 8-benzyloxy-5-[R-1-hydroxy-2-(2,3,4,7-tetrahydro-1H-inden-2-ylamino)ethyl]-1H-quinolin-2-one (0.212 g, 0.49 mmol) in ethanol (10 ml) and the resulting suspension stirred under 0.35 bar hydrogen atmosphere for 1 hour. The reaction mixture is filtered through a Celite™ filter plug, evaporated and purified by flash column chromatography (10:1 dichloromethane-methanol elution) to afford 8-hydroxy-5-[R-1-hydroxy-2-(2,3,4,7-tetrahydro-1H-inden-2-ylamino)-ethyl]-1H-quinolin-2-one, H+339.

Example 30

5-[R-2-(5,6-Diethyl-2,3,4,7-tetrahydro-1H-inden-2-ylamino)-1-hydroxyethyl]-8-hydroxy-1H-quinolin-2-one (a) Liquid ammonia (50 ml) is condensed at −78° C. and 2-amino-5,6-diethylindane (WO 0075114; 1 g, 4.43 mmol) is added, followed by lithium wire (0.615 g, 88 mmol) portionwise over 5 minutes. The reaction is stirred at −78° C. for 3 hours, then cautiously quenched with ethanol (100 ml) and warmed to ambient temperature overnight. Water is added, the mixture is extracted with ether and the combined organic extracts are washed with brine, dried (MgSO$_4$) and evaporated to afford 5,6-diethyl-2,3,4,7-tetrahydro-1H-inden-2-ylamine. $\delta_H$ 0.95 (t J 7.3 6H), 1.95-2.10 (m 2H), 2.08 (q J 4H), 2.6 (m 6H), 3.65 (m 1H)

(b) 5,6-Diethyl-2,3,4,7-tetrahydro-1H-inden-2-ylamine is reacted with 8-benzyloxy-5-R-oxiranyl-1H-quinolin-2-one using the procedure described in Example 29(b) to yield 8-benzyloxy-5-[R-2-(5,6-diethyl-2,3,4,7-tetrahydro-1H-inden-2-ylamino)-1-hydroxy-ethyl]-1H-quinolin-2-one, MH+485.

(c) 8-Benzyloxy-5-[R-2-(5,6-diethyl-2,3,4,7-tetrahydro-1H-inden-2-ylamino)-1-hydroxy-ethyl]-1H-quinolin-2-one is deprotected using the procedure described in Example 29(c) to yield 5-[R-2-(5,6-diethyl-2,3,4,7-tetrahydro-1H-inden-2-ylamino)-1-hydroxyethyl]-8-hydroxy-1H-quinolin-2-one, MH+395.

Examples 31 and 32

8-Hydroxy-5-[R-1-hydroxy-2-(1S,2S-2-hydroxy-cyclopentylamino)ethyl]-1H-quinolin-2-one and 5-[R-2-(S-cyclopent-2-enylamino)-1-hydroxyethyl]-8-hydroxy-1H-quinolin-2-one (a) A suspension of 8-benzyloxy-5-R-oxiranyl-1H-quinolin-2-one (0.20 g, 0.68 mmol) and (1S,2S)-2-benzyloxycyclopentylamine (0.391 g, 2.0 mmol) in $CHCl_3$ (0.5 ml) is heated and the solvent allowed to evaporate. The resultant melt is heated at 110° C. for 16 hours and the crude product purified by reverse phase chromatography using a Jones Flashmaster Personal™ flash chromatography system with gradient elution 0-30% acetonitrile-water containing 0.1% trifluoroacetic acid to afford 8-benzyloxy-5-[R-2-(1S,2S-2-benzyloxy-cyclopentylamino)-1-hydroxy-ethyl]-1H-quinolin-2-one trifluoroacetate. MH+485.

(b) Concentrated hydrochloric acid (1 ml) is added to a solution of 8-benzyloxy-5-[R-2-(1R,2R-2-benzyloxy-cyclopentylamino)-1-hydroxy-ethyl]-1H-quinolin-2-one trifluoroacetate (0.306 g, 0.51 mmol) in ethanol (2 ml) and the mixture is heated at reflux for 48 hours. The residue is diluted with methanol, the solvent is evaporated and the crude product is purified by reverse phase chromatography using a Jones Flashmaster Personal™ flash chromato-graphy system with gradient elution 0-50% acetonitrile-water containing 0.1% trifluoro-acetic acid to afford two products, 8-hydroxy-5-[R-1-hydroxy-2-(1S,2S-2-hydroxy-cyclo-pentylamino)ethyl]-1H-quinolin-2-one trifluoroacetate (MH+305) and 5-[R-2-(S-cyclopent-2-enylamino)-1-hydroxyethyl]-8-hydroxy-1H-quinolin-2-one trifluoroacetate. (MH+ 287).

Example 33

5-[R-2-(1S,2S-2-Cyclohexylcyclopentylamino)-1-hydroxyethyl]-8-hydroxy-1H-quinolin-2-one and 5-[R-2-(1R,2R-2-cyclohexylcyclopentylamino)-1-hydroxyethyl]-8-hydroxy-1H-quinolin-2-one (a) A suspension of 8-benzyloxy-5-R-oxiranyl-1H-quinolin-2-one (0.110 g, 0.38 mmol) and (±) cis-2-cyclohexylcyclopentylamine (J. Med. Chem., 1973, 16, 679; 0.125 g, 0.76 mmol) in $CHCl_3$ (0.5 ml) is heated and the solvent allowed to evaporate. The resultant melt is heated at 80° C. for 24 hours and the crude product purified by reverse phase chromatography, eluting with gradient 0-50% acetonitrile-water containing 0.1% trifluoroacetic acid to afford a mixture of 8-benzyloxy-5-[R-2-(1S,2S,2-cyclohexylcyclopentyl-amino)-1-hydroxy-ethyl]-1H-quinolin-2-one and 8-benzyloxy-5-[R-2-(1R,2R-2-cyclohexyl-cyclo-pentylamino)-1-hydroxy-ethyl]-1H-quinolin-2-one. $\delta_H$ 0.90-2.0 (m 18H), 2.50-3.10 (m 3H), 5.0-5.10 (m 1H), 5.12 (s 2H), 6.60 (d J 6 1H) 6.90-7.40 (m 7H), 8.02 (m 1H), 9.10 (br s 1H)

(b) These compounds are deprotected using the procedure described in Example 29(c) to yield a mixture of 5-[R-2-(1S,2S-2-cyclohexylcyclopentylamino)-1-hydroxyethyl]-8-hydroxy-1H-quinolin-2-one and 5-[R-2-(1R,2R-2-cyclohexylcyclopentylamino)-1-hydroxyethyl]-8-hydroxy-1H-quinolin-2-one (MH+371).

Example 34

5-[R-2-(1R,2R-bicyclopentyl-2-ylamino)-1-hydroxyethyl]-8-hydroxy-1H-quinolin-2-one (a) A mixture of 8-benzyloxy-5-R-oxiranyl-1H-quinolin-2-one (0.200 g, 0.68 mmol) and 1R, 2R-bicyclopentyl-2-ylamine (Eur. J. Med. Chem., 2000, 35, 377; 0.209 g, 1.36 mmol) in N,N-dimethylacetamide (2 ml) in a closed vial is irradiated in a CEM™ microwave reactor at 150 W (180° C.) for 8 minutes. The crude product purified by reverse phase chromatography, eluting with gradient 0-50% acetonitrile-water containing 0.1% trifluoroacetic acid to afford 8-benzyloxy-5-[R-2-(1R,2R-bicyclopentyl-2-ylamino)-1-hydroxyethyl]-1H-quinolin-2-one. HPLC retention time 0.821 minutes.

(b) 8-Benzyloxy-5-[R-2-(1R,2R-bicyclopentyl-2-ylamino)-1-hydroxyethyl]-1H-quinolin-2-one (0.10 g, 0.22 mmol) and 10% Pd/C (50 mg) are suspended in methanol (4 ml) in a Radleys Carousel™ reaction station The mixture is stirred under hydrogen atmosphere (0.35 bar) for 2 hours, the catalyst filtered on a Celite™ filter bed and washed with methanol. The combined filtrate and washings are evaporated and purified by MS directed preparative HPLC to afford 5-[R-2-(1R,2R-bicyclopentyl-2-ylamino)-1-hydroxyethyl]-8-hydroxy-1H-quinolin-2-one. MH+357.

Example 35

5-[R-2-(1R,2R-2-Benzylcyclopentylamino)-1-hydroxyethyl]-8-hydroxy-1H-quinolin-2-one (a) 1R,2R-2-Benzylcyclopentylamine is prepared using the procedure described in Eur. J. Med. Chem., 2000, vol 35, 377.

(b) 1R,2R-2-Benzylcyclopentylamine is reacted with 8-benzyloxy-5-R-oxiranyl-1H-quinolin-2-one using the procedure described in Example 35(a) to yield 5-[R-2-(1R,2R-2-benzylcyclo-pentylamino)-1-hydroxy-ethyl]-8-benzyloxy-1H-quinolin-2-one. HPLC retention time 0.843 min.

(c) 5-[R-2-(1R,2R-2-Benzylcyclo-pentylamino)-1-hydroxy-ethyl]-8-benzyloxy-1H-quinolin-2-one is deprotected using the procedure described in Example 35(b) to yield 5-[R-2-(1R,2R-2-benzylcyclopentylamino)-1-hydroxyethyl]-8-hydroxy-1H-quinolin-2-one, MH+377.

Examples 36 to 42

The compounds of these Examples are prepared using procedures that are analogous to those described in Examples 29 to 35 respectively except using 7-benzyloxy-5-R-oxiranyl-3,4-dihydro-1H-quinolin-2-one in place of 8-benzyloxy-5-R-oxiranyl-1H-quinolin-2-one.

Examples 43 to 48

The compounds of these Examples are prepared using procedures that are analogous to those described in Example 29.

Examples 49 to 54

The compounds of these Examples are prepared using procedures that are analogous to those described in Example 29 except using 7-benzyloxy-5-R-oxiranyl-3,4-dihydro-1H-quinolin-2-one in place of 8-benzyloxy-5-R-oxiranyl-1H-quinolin-2-one.

Especially preferred compounds of formula I include compounds of formula XXXV as hereinbefore defined wherein $R^1$, $R^2$ and T are as shown in Table 3 below, the method of preparation being described hereinafter. The compound of Example 55 is prepared as a trifluoroacetate salt. 1H NMR spectra are recorded at 400 MHz in $CDCl_3$ unless otherwise noted. Mass spectra are obtained under electrospray ionisation conditions with LC gradient elution of 5% to 95% acetonitrile-water in the presence of 0.1% formic acid.

TABLE 3

| Ex | $R^1$ | $R^2$ | T | MH+ |
|---|---|---|---|---|
| 55 | —OH | —H | 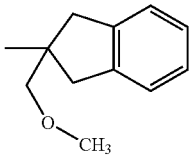 | 381 |
| 56 | —OH | —H | 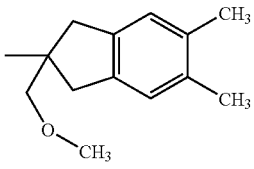 | — |
| 57 | —OH | —H | 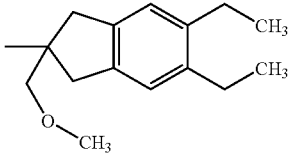 | — |
| 58 | —OH | —H | 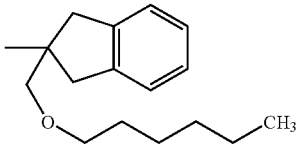 | — |
| 59 | —OH | —H | 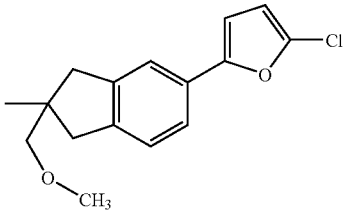 | — |
| 60 | —OH | —H | 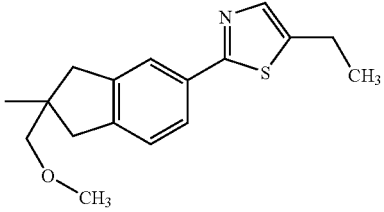 | — |
| 61 | —OH | —H | 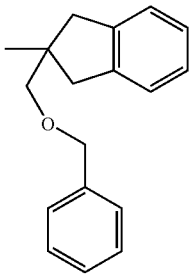 | — |

TABLE 3-continued

| Ex | R¹ | R² | T | MH+ |
|----|----|----|---|-----|
| 62 | —H | —OH | 2-methyl-2-(methoxymethyl)-2,3-dihydro-1H-indene | — |
| 63 | —H | —OH | 2-methyl-2-(methoxymethyl)-5,6-dimethyl-2,3-dihydro-1H-indene | — |
| 64 | —H | —OH | 2-methyl-2-(methoxymethyl)-5,6-diethyl-2,3-dihydro-1H-indene | — |
| 65 | —H | —OH | 2-methyl-2-(hexyloxymethyl)-2,3-dihydro-1H-indene | — |
| 66 | —H | —OH | 2-methyl-2-(methoxymethyl)-5-(5-chlorofuran-2-yl)-2,3-dihydro-1H-indene | — |
| 67 | —H | —OH | 2-methyl-2-(methoxymethyl)-5-(5-ethylthiazol-2-yl)-2,3-dihydro-1H-indene | — |
| 68 | —H | —OH | 2-methyl-2-(benzyloxymethyl)-2,3-dihydro-1H-indene | — |

TABLE 3-continued
| Ex | R¹ | R² | T | MH+ |
|---|---|---|---|---|
| 69 | —OH | —H | 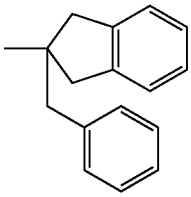 | — |
| 70 | —OH | —H | 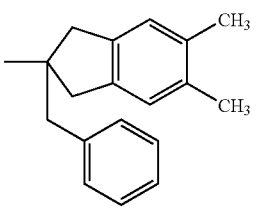 | — |
| 71 | —OH | —H | 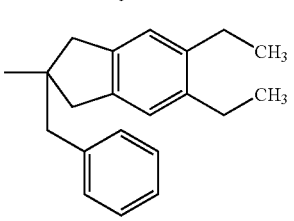 | — |
| 72 | —OH | —H | 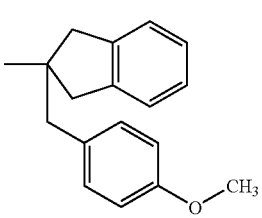 | — |
| 73 | —OH | —H | 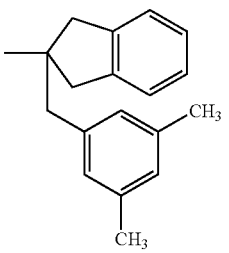 | — |
| 74 | —OH | —H | 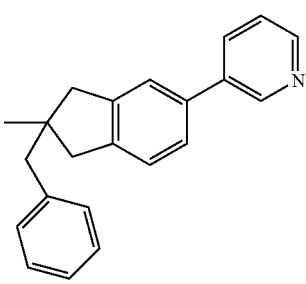 | — |
| 75 | —H | —OH | 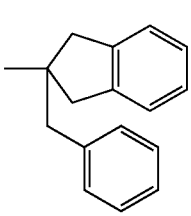 | — |

TABLE 3-continued

| Ex | R¹ | R² | T | MH+ |
|----|----|----|---|-----|
| 76 | —H | —OH | 1-benzyl-2-methyl-5,6-dimethylindan | — |
| 77 | —H | —OH | 1-benzyl-2-methyl-5,6-diethylindan | — |
| 78 | —H | —OH | 2-methyl-1-(4-methoxybenzyl)indan | — |
| 79 | —H | —OH | 2-methyl-1-(3,5-dimethylbenzyl)indan | — |
| 80 | —H | —OH | 2-benzyl-2-methyl-5-(pyridin-3-yl)indan | — |

Example 55

8-Hydroxy-5-[R-1-hydroxy-2-(2-methoxymethylindan-2-ylamino)-ethyl]-1H-quinolin-2-one (a) Lithium aluminium hydride (1 M solution in ether, 23.7 ml, 23.7 mmol) is added to a solution of 2-aminoindan-2-carboxylic acid (*J. Med. Chem.* 1991, 34, 3125; 2.26 g, 12.8 mmol) in ether (150 ml). The reaction is stirred for 2 hours at ambient temperature and quenched sequentially with water (0.9 ml), 2 M NaOH (0.9 ml) and further water (0.9 ml). MgSO₄ is added and the resultant suspension is filtered. The filtrate is evaporated to afford (2-aminoindan-2-yl)methanol, MH+164.

(b) A mixture of (2-aminoindan-2-yl)methanol (0.407 g, 2.50 mmol) and phthalic anhydride (0.369 g, 2.50 mmol) is heated at 160° C. for 40 minutes. The reaction mixture is poured into water and extracted with chloroform. The organic phase is dried (Na₂SO₄) and evaporated to afford 2-(2-hydroxymethylindan-2-yl)-isoindole-1,3-dione, MH+294.

(c) (Trimethylsilyl)diazomethane (2 M hexanes, 0.51 ml, 1.03 mmol) is added dropwise to a cooled (0° C.) solution of 2-(2-hydroxymethylindan-2-yl)-isoindole-1,3-dione (0.150 g, 0.511 mmol) and fluoroboric acid (48% aqueous, 93.5 μl, 0.511 mmol) in CH₂Cl₂ (4 ml). The reaction is stirred for 20 minutes, then three further portions of (trimethylsilyl)diazomethane (2 M hexanes, 0.128 ml, 0.25 mmol; 64 μl, 0.12 mol; 64 μl, 0.12 mmol)) are made at 20 minute intervals. The reaction is stirred for a further 40 minutes after the final addition, poured into water and extracted with dichloromethane. The organic phase is washed with brine, dried (MgSO$_4$) and evaporated. The crude product is purified by flash chromatography (CH$_2$Cl$_2$ elution) to afford 2-(2-methoxymethylindan-2-yl)-isoindole-1,3-dione, MH+308.

(d) A mixture of 2-(2-methoxymethylindan-2-yl)-isoindole-1,3-dione (0.30 g, 0.976 mmol) and hydrazine hydrate (47 µl, 0.976 mmol) in 95% ethanol (15 ml) is heated to reflux for 45 hours. Further hydrazine hydrate (9.4 µl, 0.976 mmol) is added and the reaction refluxed for an additional 16 hours, followed by addition of a final portion of hydrazine hydrate (9.4 µl, 0.976 mmol) and a further 16 hours reflux. After cooling, the resultant suspension is filtered and the filter cake washed with ethanol. The combined filtrate and washings are evaporated and triturated with ether to afford 2-methoxymethylindan-2-ylamine, MH+178.

(e) A mixture of 2-methoxymethylindan-2-ylamine (0.140 g, 0.790 mmol) and 8-benzyloxy-5-R-oxiranyl-1H-quinolin-2-one (0.154 g, 0.527 mmol) in 2-methoxyethyl ether (2.5 ml) is degassed by bubbling argon for 5 minutes then heated in a sealed tube at 190° C. for 60 hours. The solvent is evaporated and the crude product purified by flash chromatography (20:1 CH$_2$Cl$_2$/MeOH elution) to afford 8-benzyloxy-5-[R-1-hydroxy-2-(2-methoxymethylindan-2-ylamino)-ethyl]-1H-quinolin-2-one, MH+471.

(e) A mixture of 8-benzyloxy-5-[R-1-hydroxy-2-(2-methoxymethylindan-2-ylamino)-ethyl]-1H-quinolin-2-one (50 mg, 0.106 mmol) and 10% Pd/C (19 mg) in ethanol (5 ml) is hydrogenated at 0.35 bar for 4 hours. The reaction mixture is filtered and the filtrate evaporated. The residue is purified by preparative HPLC to afford 8-hydroxy-5-[R-1-hydroxy-2-(2-methoxymethylindan-2-ylamino)-ethyl]-1H-quinolin-2-one trifluoroacetate, MH+381.

Examples 56 to 61

The compounds of these Examples are prepared analogously to Example 55.

Examples 62 to 68

The compounds of these Examples are prepared using procedures that are analogous to those described in Example 55 except using 7-benzyloxy-5-R-oxiranyl-3,4-dihydro-1H-quinolin-2-one in place of 8-benzyloxy-5-R-oxiranyl-1H-quinolin-2-one.

Example 69

5-[R-2-(2-Benzylindan-2-ylamino)-1-hydroxyethyl]-8-hydroxy-1H-quinolin-2-one (a) K$_3$Fe(CN)$_6$ (18.0 g, 54.8 mmol) is added to hot (80° C.) degassed water (150 ml), followed by 2-benzylindan-1-one (J. Mol. Catal. A 2000, 154, 237; 3.8 g, 17.1 mmol). Concentrated aqueous ammonia (14 ml) is then added over 15 minutes and the reaction mixture heated at 80-90° C. in the dark for 24 hours. After cooling to ambient temperature, the mixture is extracted with chloroform. The combined chloroform extracts are extracted with 3 M HCl and the acidic extracts are evaporated to afford 2-amino-2-benzylindan-1-one hydrochloride, MH+238.

(b) Trifluoroacetic anhydride (0.763 ml, 5.4 mmol) is added to a cooled (0° C.) solution of 2-amino-2-benzylindan-1-one hydrochloride (1.0 g, 3.65 mmol) and triethylamine (1.27 ml, 9.13 mmol) in tetrahydrofuran (THF) (50 ml). The cooling bath is removed and the reaction is stirred at ambient temperature for 4 hours. Additional trifluoroacetic anhydride (0.102 ml, 0.73 mmol) is added and the reaction stirred for 16 hours. The solvent is evaporated and the residue partitioned between ether and 1 M HCl. The organic phase is washed with brine, dried (MgSO$_4$) and evaporated to afford N-(2-benzyl-1-oxoindan-2-yl)-2,2,2-trifluoro-acetamide, MH+334.

(c) A mixture of N-(2-benzyl-1-oxoindan-2-yl)-2,2,2-trifluoroacetamide (0.200 g, 0.60 mmol), 10% Pd/C (50 mg) and concentrated H$_2$SO$_4$ (30 µl) in acetic acid (13.3 ml) is hydrogenated at 0.35 bar for 1 hour. Further concentrated H$_2$SO$_4$ (10 µl) is added and the hydrogenation is continued for 16 hours. The reaction is filtered, the filtrate is evaporated and the residue partitioned between ethyl acetate and water. The aqueous phase is basified to pH 11 with 1 M aqueous NaOH and extracted with ethyl acetate. The organic extract is washed with brine, dried (MgSO$_4$) and evaporated to afford 2-benzylindan-2-ylamine, MH+ 224.

(d) A mixture of 2-benzylindan-2-ylamine (55 mg, 0.246 mmol) and 8-benzyloxy-5-R-oxiranyl-1H-quinolin-2-one (48 mg, 0.164 mmol) in 2-methoxyethyl ether (2 ml) is degassed by bubbling argon for 5 minutes then heated in a sealed tube at 190° C. for 40 hours. The solvent is evaporated and the crude product purified by flash chromatography (25:1 CH$_2$Cl$_2$/MeOH elution) to afford 5-[R-2-(2-benzylindan-2-ylamino)-1-hydroxyethyl]-8-benzyloxy-1H-quinolin-2-one, MH+517.

(e) A mixture of 5-[R-2-(2-benzylindan-2-ylamino)-1-hydroxyethyl]-8-benzyloxy-1H-quinolin-2-one (22 mg, 0.04 mmol) and 10% Pd/C (10 mg) in ethanol (7 ml) is hydrogenated at 0.35 bar for 9 hours. The reaction mixture is filtered and the filtrate evaporated to afford 5-[(R)-2-(2-benzylindan-2-ylamino)-1-hydroxyethyl]-8-hydroxy-1H-quinolin-2-one, MH+427.

Examples 70 to and 74

These compounds are prepared analogously to Example 69.

Examples 75 to 80

The compounds of these Examples are prepared using procedures that are analogous to those described in Example 69 except using 7-benzyloxy-5-R-oxiranyl-3,4-dihydro-1H-quinolin-2-one in place of 8-benzyloxy-5-R-oxiranyl-1H-quinolin-2-one.

Especially preferred compounds of formula I include compounds of formula XXXV as hereinbefore defined wherein $R^1$, $R^2$ and T are as shown in Table 4 below, the method of preparation being described hereinafter. 1H NMR spectra are recorded at 400 MH in CDCl$_3$ unless otherwise noted and 13C NMR spectra are recorded at 100 MHz. Mass spectra are obtained under electrospray ionisation conditions with LC gradient elution of 5% to 95% acetonitrile-water in the presence of 0.1% formic acid. Preparative LCMS is conducted on a Phenomenex Luna C$_{18}$ column (50×21.2 mm, 10 µM particle size).

TABLE 4

| Ex | R¹ | R² | T | MH+ |
|---|---|---|---|---|
| 81 | —OH | —H | | 454 |
| 82 | —OH | —H | | — |
| 83 | —OH | —H | | — |
| 84 | —OH | —H | | — |
| 85 | —OH | —H | | — |
| 86 | —OH | —H | | — |
| 87 | —OH | —H | | — |
| 88 | —OH | —H | | — |
| 89 | —OH | —H | | — |
| 90 | —OH | —H | | — |

TABLE 4-continued

| Ex | R¹ | R² | T | MH+ |
|---|---|---|---|---|
| 91 | —OH | —H | | — |
| 92 | —OH | —H | | — |
| 93 | —OH | —H | | — |
| 94 | —OH | —H | | — |
| 95 | —OH | —H | | — |
| 96 | —OH | —H | | — |
| 97 | —OH | —H | | 352 |
| 98 | —OH | —H | | — |
| 99 | —OH | —H | | — |
| 100 | —OH | —H | | — |
| 101 | —OH | —H | | — |
| 102 | —OH | —H | | — |
| 103 | —OH | —H | | — |

TABLE 4-continued
| Ex | R¹ | R² | T | MH+ |
|----|----|----|---|-----|
| 104 | —OH | —H | 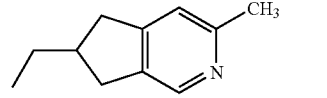 | — |
| 105 | —OH | —H | 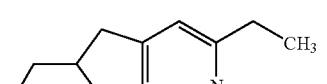 | — |
| 106 | —OH | —H | 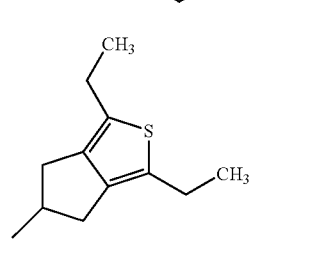 | — |
| 107 | —OH | —H | 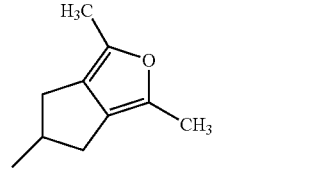 | — |
| 108 | —OH | —H | 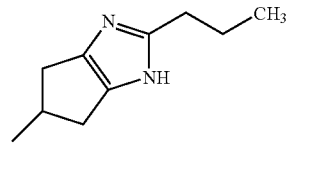 | — |
| 109 | —OH | —H | 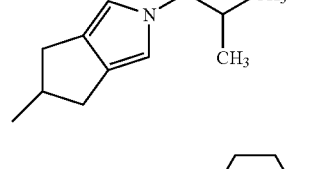 | — |
| 110 | —H | —OH | 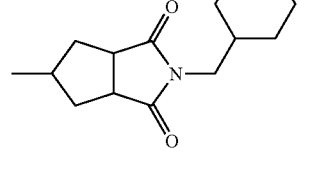 | — |
| 111 | —H | —OH | 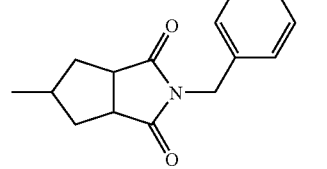 | — |
| 112 | —H | —OH | 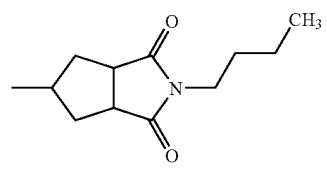 | — |
| 113 | —H | —OH | 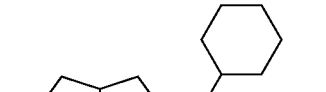 | — |
| 114 | —H | —OH | 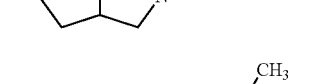 | — |
| 115 | —H | —OH | 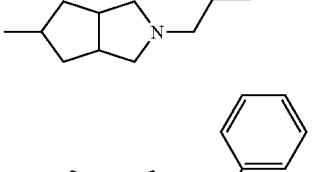 | — |
| 116 | —H | —OH | 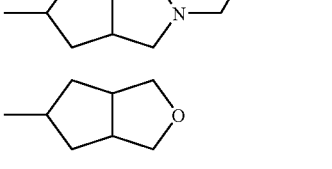 | — |
| 117 | —H | —OH | 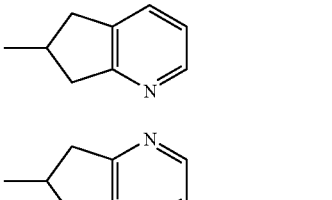 | — |
| 118 | —H | —OH | 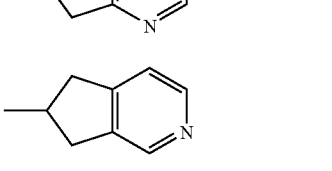 | — |
| 119 | —H | —OH | 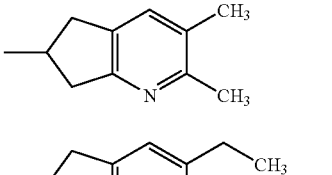 | — |
| 120 | —H | —OH | 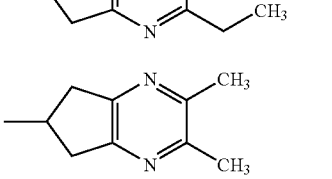 | — |
| 121 | —H | —OH | 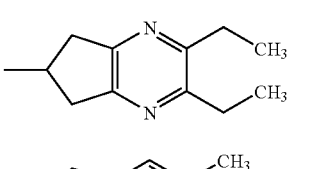 | — |
| 122 | —H | —OH | 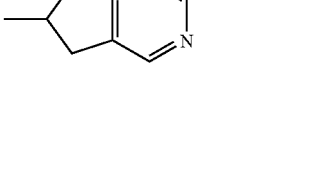 | — |
| 123 | —H | —OH |  | — |
| 124 | —H | —OH |  | — |

TABLE 4-continued

| Ex | R¹ | R² | T | MH+ |
|---|---|---|---|---|
| 125 | —H | —OH | (structure) | — |
| 126 | —H | —OH | (structure) | — |
| 127 | —H | —OH | (structure) | — |
| 128 | —H | —OH | (structure) | — |
| 129 | —H | —OH | (structure) | — |
| 130 | —H | —OH | (structure) | — |
| 131 | —H | —OH | (structure) | — |
| 132 | —H | —OH | (structure) | — |
| 133 | —H | —OH | (structure) | — |
| 134 | —H | —OH | (structure) | — |
| 135 | —H | —OH | (structure) | — |
| 136 | —H | —OH | (structure) | — |
| 137 | —H | —OH | (structure) | — |
| 138 | —H | —OH | (structure) | — |

Example 81

(3aS,5R,6aR)-2-Cyclohexylmethyl-5-[R-2-hydroxy-2-(8-hydroxy-2-oxo-1,2-dihydroquinolin-5-yl)ethylamino]tetrahydrocyclopenta[c]pyrrole-1,3-dione and (3aS,5S,6aR)-2-cyclohexyl-methyl-5-[R-2-hydroxy-2-(8-hydroxy-2-oxo-1,2-dihydroquinolin-5-yl)ethylamino]tetra-hydrocyclopenta[c]pyrrole-1,3-dione (a) A mixture of (7S,8R)-1,4-dioxaspiro[4.4]nonane-7,8-dicarboxylic acid dimethyl ester (*J Org Chem*, 1989, 54, 5115; 1.0 g, 4.09 mmol) and benzylamine (6 ml) is heated in a sealed tube at 195° C. for 16 hours. The benzylamine is evaporated and the residue purified by flash chromatography, eluting with 2:1 isohexanes-ethyl acetate (EtOAc) to afford (3aS,6aR)-2-benzylspiro[tetrahydrocyclopenta[c]pyrrole-5(1H), 2'-[1,3]dioxolane]-1,3-dione, MH+288

(b) 1M aqueous hydrochloric acid (3 ml) is added portionwise to a refluxing solution of (3aS,6aR)-2-benzylspiro[tetrahydrocyclopenta[c]pyrrole-5(1H), 2'-[1,3]dioxolane]-1,3-dione (0.265 g, 0.92 mmol) in acetone (20 ml). The reaction is heated for 16 hours, the solvent evaporated and the residue partitioned between dichloromethane and water. The organic phase is washed with brine, dried (MgSO₄) and evaporated. The crude product is purified by flash chromatography, eluting with neat dichloromethane to afford (3aS,6aR)-2-benzyl-tetrahydrocyclopenta[c]pyrrole-1,3,5-trione, MH+244.

(c) Sodium acetate (0.121 g, 0.89 mmol) is added to a suspension of (3aS,6aR)-2-benzyl-tetrahydrocyclopenta[c]pyrrole-1,3,5-trione (90 mg, 0.37 mmol) in ethanol (3 ml), followed by hydroxylamine hydrochloride (62 mg, 0.89 mmol) and water (1 ml). The reaction is heated to reflux for 1 hour and evaporated. The residue is partitioned between water and EtOAc, the organic phase is washed with brine, dried (MgSO₄) and evaporated to afford (3aR,6aS)-2-benzyl-tetrahydrocyclopentatcpyrrole-1,3,5-trione 5-oxime, MH+259.

(d) A suspension of (3aR,6aS)-2-benzyl-tetrahydrocyclopenta[c]pyrrole-1,3,5-trione 5-oxime (86 mg, 0.33 mmol), platinum oxide (19 mg) and concentrated hydrochloric acid (0.2 ml) in ethanol (10 ml) is hydrogenated at 0.35 bar for 16 hours. The reaction mixture is filtered and the filtrate evaporated. The residue is partitioned between saturated aqueous sodium bicarbonate and EtOAc, the organic phase is washed with brine, dried (Na₂SO₄) and evaporated to afford a mixture of (3aR,5R, 6aS)-5-amino-2-cyclohexylmethyl-tetrahydrocyclopenta[c]pyrrole-1,3-dione and (3aR,5S, 6aS)-5-amino-2-cyclohexcylmethyl-tetrahydro-cyclopenta[c]pyrrole-1,3-dione, MH+251.

(e) N,O-Bis(trimethysilyl)acetamide (33.5 µl, 0.20 mmol) is added to a suspension of (3aR,5R, 6aS)-5-amino-2-cyclohexylmethyl-tetrahydrocyclopenta[c]pyrrole-1,3-dione and (3aR,5S, 6aS)-5-amino-2-cyclohexylmethyl-tetrahydrocyclopenta[c]pyrrole-1,3-dione (68 mg, 0.27 mmol) in N,N-dimethylformamide (DMF) (1 ml), followed 30 minutes later by 8-benzyloxy-5-R-oxiranyl-1H-quinolin-2-one (53 mg, 0.18 mmol). The reaction is heated at 90° C. for 4 days. The solvent is evaporated and the residue purified by flash chromatography, eluting with EtOAc-2% MeOH/EtOAc gradient to afford a mixture of (3aS,5R,6aR)-5-[R-2-(8-benzyloxy-2-oxo-1,2-dihydro-quinolin-5-yl)-2-hydroxy-ethylamino]-2-cyclohexylmethyl-tetrahydrocyclopenta[c]pyrrole-1,3-dione and (3aS,5S,6aR)-5-[R-2-(8-benzyloxy-2-oxo-1,2-dihydro-quinolin-5-yl)-2-hydroxy-ethylamino]-2-cyclohexylmethyltetrahydrocyclopenta[c]-pyrrole-1,3-dione, MH+544.

(f) A suspension of (3aS,5R,6aR)-5-[R-2-(8-benzyloxy-2-oxo-1,2-dihydro-quinolin-5-yl)-2-hydroxy-ethylamino]-2-cyclohexylmethyltetrahydrocyopenta[c]pyrrole-1,3-dione and (3aS,5S,6aR)-5-[R-2-(8-benzyloxy-2-oxo-1,2-dihydro-quinolin-5-yl)-2-hydroxy-ethylamino]-2-cyclohexylmethyltetrahydrocyclopenta[c]pyrrole-1,3-dione (29 mg, 0.05 mmol) and 10% Pd/C (11 mg) in MeOH (10 ml) is hydrogenated at 0.35 bar for 50 minutes. The reaction mixture is filtered through a Celite™ plug, washed with MeOH and the filtrate and washings are evaporated. The crude product is purified by preparative thin layer chromatography (multiple elutions with EtOAc) to afford a mixture of (3aS,5R,6aR)-2-cyclohexylmethyl-5-[R-2-hydroxy-2-(8-hydroxy-2-oxo-1,2-dihydroquinolin-5-yl)ethylamino]tetrahydro-cyclopenta[c]pyrrole-1,3-dione and (3aS,5S,6aR)-2-cyclohexylmethyl-5-[R-2-hydroxy-2-(8-hydroxy-2-oxo-1,2-dihydroquinolin-5-yl)ethylamino]tetrahydrocyclopenta[c]pyrrole-1,3-dione, MH+454.

Examples 82 to 84

These compounds are prepared using procedures analogous to those used in Example 81 using the appropriate amine.

Example 85

5-[R-2-((3aS,5R,6aR)-2-Butyloctahydrocyclopenta [c]pyrrol-5-ylamino)-1-hydroxyethyl]-8-hydroxy-1H-quinolin-2-one and 5-[R-2-((3aS,5S,6aR)-2-butyloctahydrocyclopenta[c]pyrrol-5-ylamino)-1-hydroxyethyl]-8-hydroxy-1H-quinolin-2-one (a) Methanesulfonyl chloride (1.93 ml, 24.9 mmol) is added to a cooled (0° C.) solution of ((7R,8S)-8-hydroxymethyl-1,4-dioxa-spiro[4.4]non-7-yl)-methanol (*Tet. Lett.*, 2002,43, 4947; 1.17 g, 6.22 mmol) and triethylamine (3.50 ml, 24.9 mmol) in dichloromethane (30 ml). The reaction is stirred for 2 hours at 0° C. and then partitioned between dichloromethane and iced water. The organic phase is washed with 1M aqueous HCl, saturated aqueous NaHCO₃, brine, dried (MgSO₄) and evaporated to afford methanesulfonic acid (7R,8S)-8-methane-sulfonyloxymethyl-1,4-dioxaspiro [4.4]non-7-ylmethyl ester, MH+345.

(b) A suspension of methanesulfonic acid (7R,8S)-8-methanesulfonyloxymethyl-1,4-dioxaspiro-[4.4]non-7-ylmethyl ester (0.250 g, 0.73 mmol) in n-butylamine (1 ml) is heated at 90° C. for 3 hours. The reaction is evaporated and partitioned between EtOAc and 2M aqueous NaOH. The organic phase is washed with brine, dried (MgSO₄) and evaporated. The crude product is purified by flash chromatography, eluting with EtOAc to afford (3aR,6aS)-2-butylspiro[hexahydrocyclopenta[c]pyrrole-5(1H),2'-[1,3]dioxolane], M+226.

(c) A solution of (3aR,6aS)-2-butylspiro[tetrahydrocyclopenta[c]pyrrole-5(1H),2'-[1,3]dioxo-lane] (1.02 g, 45.3 mmol) in 0.5M aqueous HCl is stirred at ambient temperature for 16 hours. After washing with ether, 2M aqueous NaOH is added and the mixture is extracted with EtOAc. The organic phase is washed with brine, dried (MgSO₄) and evaporated to afford (3aS,6aR)-2-butylhexahydrocyclopenta[c]pyrrol-5-one, MH+182.

(d) A suspension of (3aS,6aR)-2-butylhexahydrocyclopenta[c]pyrrol-5-one (0.467 g, 2.58 mmol), hydroxylamine hydrochloride (0.430 g, 6.19 mmol) and sodium acetate (0.842 g, 6.19 mmol) in ethanol (21 ml) and water (7 ml) is heated to reflux for 1 hour. The ethanol is evaporated and the residue partitioned between saturated aqueous NaHCO₃ and EtOAc. The organic phase is washed with brine, dried (MgSO₄) and evaporated to afford (3aS,6aR)-2-butylhexahydrocyclopenta[c]pyrrol-5-one oxime, MH+197.

(e) Concentrated HCl (1.2 ml) is added to a solution of (3aS,6aR)-2-butylhexahydrocyclo-penta[c]pyrrol-5-one oxime (0.306 g, 1.56 mmol) in ethanol, followed by platinum oxide (84 mg) and the suspension is hydrogenated at 0.35 bar for 16 hours. Further portions of platinum oxide (2×80 mg) are added until the reaction is complete after a total of 4 days. Water (20 ml) is added, the catalyst is filtered off and the filtrate evaporated to remove ethanol. The residue is treated with 1M aqueous NaOH and extracted with ether. The organic phase is washed with water, brine, dried (MgSO₄) and evaporated to afford a mixture of (3aS,5R,6aR)-2-butyloctahydrocyclopenta[c]pyrrol-5-ylamine and (3aS,5S,6aR)-2-butyloctahydrocyclopenta[c]pyrrol-5-ylamine, MH+183.

(f) N,O-Bis(trimethysilyl)acetamide (0.108 ml, 0.66 mmol) is added to a solution of (3aS,5R,6aR)-2-butyloctahydrocyclopenta[c]pyrrol-5-ylamine and (3aS,5S,6aR)-2-butyloctahydrocyclopenta[c]pyrrol-5-ylamine (0.159 g, 0.84 mmol) in DMF (1.5 ml), followed 30 minutes later by 8-benzyloxy-5-R-oxiranyl-1H-quinolin-2-one (0.171 g, 0.87 mmol). The reaction is heated at 90° C. for 16 hours and the solvent is evaporated. The residue is triturated with EtOAc and the supernatant liquors diluted with hexane, left to evaporate and triturated with ether. The crude product is purified by flash chromatography (12:1 dichloromethane/MeOH-1:1 MeOH/ammonia gradient elution) to afford a mixture of 8-benzyloxy-5-[R-2-((3aS,5R,6aR)-2-butyloctahydrocyopenta[c]pyrrol-5-ylamino)-1-hydroxyethyl]-1H-quinolin-2-one and 8-benzyloxy-5-[R-2-((3aS,5S,6aR)-2-butyloctahydro-cyclopenta[c]pyrrol-5-ylamino)-1-hydroxyethyl]-1H-quinolin-2-one, MH+476.

(g) A mixture of 8-benzyloxy-5-[R-2-((3aS,5R,6aR)-2-butyloctahydrocyclopenta[c]pyrrol-5-ylamino)-1-hydroxyethyl]-1H-quinolin-2-one and 8-benzyloxy-5-[R-2-((3aS,5S, 6aR)-2-butyloctahydrocydopenta[c]pyrrol-5-ylamino)-1-hydroxyethyl]-1H-quinolin-2-one (38 mg, 0.08 mmol) and 10% Pd/C (20 mg) in MeOH (10 ml) is hydrogenated at 0.35 bar for 45 minutes. The reaction mixture is filtered through a Celite™ filter plug, washed with MeOH and the combined filtrate and washings evaporated. The residue is redissolved in MeOH and ether is added to precipitate a solid. The supernatant liquor is evaporated to afford a mixture of 5-[R-2-((3aS, 5R,6aR)-2-butyloctahydrocyclopenta[c]pyrrol-5-ylamino)-1-hydroxyethyl]-8-hydroxy-1H-quinolin-2-one and 5-[R-2-

((3aS,5S,6aR)-2-butyloctahydro-cyclopenta[c]pyrrol-5-ylamino)-1-hydroxyethyl]-8-hydroxy-1H-quinolin-2-one, MH+386.

Examples 86 and 87

These compounds are prepared using procedures analogous to those used in Example 85 using the appropriate amine.

Example 88

5-{R-2-[R-(6,7-Dihydro-5H-[1]pyrindin-6-yl)amino]-1-hydroxyethyl}-8-hydroxy-1H-quinolin-2-one and 5-{R-2-[S-(6,7 dihydro-5H-[1]pyrindin-6-yl)amino]-1-hydroxyethyl}-8-hydroxy-1H-quinolin-2-one (a) Sodium metal (0.345 g, 15.0 mmol) is dissolved in ethanol (20 ml) and diethyl malonate (0.713 g, 4.70 mmol) is added, followed by a suspension of 2,3-bis(chloromethyl)pyridine hydrochloride (*Org. Process Res. Dev.*, 2002, 6, 938; 1.0 g, 4.70 mmol) in ethanol (15 ml) over 5 minutes. The reaction is heated to reflux for 5 hours, cooled to ambient temperature and filtered. The filtrate is evaporated, taken into water and extracted with ethyl acetate. The combined organic phases are washed with brine, dried ($MgSO_4$) and evaporated. The crude product is purified by flash column chromatography (3:1-2:1 isohexanes-EtOAc gradient) to afford 5,7-dihydro-[1]pyrindine-6,6-dicarboxylic acid diethyl ester, MH+264.

(b) 5,7-Dihydro-[1]pyrindine-6,6-dicarboxylic acid diethyl ester (0.953 g, 3.62 mmol) is taken into concentrated hydrochloric acid, heated to reflux for 4 hours and evaporated to afford 6,7-dihydro-5H-[1]pyrindine-6-carboxylic acid hydrochloride. $\delta_c$ (DMSO-d6) 33.9 (t), 34.5 (t) 41.2 (d), 124.8 (d), 140.1 (d), 140.8 (d), 141.2 (s), 158.4 (s), 175.2 (s).

(c) Triethylamine (1.50 ml, 10.79 mmol) is added to a cooled (0° C.) solution of 6,7-dihydro-5H-[1]pyrindine-6-carboxylic acid hydrochloride (1.00 g, 5.02 mmol) in acetone (8 ml) and water (1.6 ml), followed by dropwise addition of ethyl chloroformate (0.721 ml, 7.54 mmol) over S minutes. The reaction is stirred at 0° C. for 50 minutes, then a solution of sodium azide (0.521 g, 8.04 mmol) in water (3 ml) is added. After 1.5 hours, the reaction is poured into brine and extracted with ether. The combined ether extracts are dried ($Na_2SO_4$) and evaporated. The residue is taken into toluene (40 ml) and gradually heated to 100° C. until gas evolution ceases. The solvent is evaporated, the residue taken into 6N hydrochloric acid and heated to reflux for 16 hours. After evaporation, the crude hydrochloride salt is taken into MeOH and polymer supported trisamine (10 g) is added, followed by decolourising charcoal. The suspension is filtered through a Celite™ filter pad and the filtrate evaporated. The resultant material is purified by flash column chromatography (20:1 $CH_2Cl_2$-MeOH containing 1% triethylamine elution) to afford 6,7-dihydro-5H-[1]pyrindin-6-ylamine. $\delta_H$ 2.65 (1H dd J 15.9 5.1), 2.74 (1H dd J 16.6 5.1), 3.15 (1H dd J 16.1 7.0), 3.23 (1H dd J 16.6 7.0), 3.83 (1H m), 6.97 (1H dd J 6.9 4.8), 7.42 (1H d J 6.9), 8.28 (1H d J 4.8).

(d) A suspension of 6,7-dihydro-5H-[1]pyrindin-6-ylamine (74 mg, 0.55 mmol) and 8-benzyloxy-5-R-oxiranyl-1H-quinolin-2-one (83 mg, 0.28 mmol) in 2-methoxyethyl ether (1.5 ml) is degassed by bubbling argon for 5 minutes, then heated in a sealed tube at 160° C. for 22 hours. The solvent is evaporated and the residue sonicated with MeOH and filtered to remove insoluble material. The filtrate is evaporated and purified by preparative LCMS (0-95% acetonitrile water containing 0.1% trifluoroacetic acid gradient) to afford a mixture of 8-benzyloxy-5-{R-2-[R-(6,7-dihydro-5H-[1]pyrindin-6-yl)amino]-1-hydroxyethyl}-1Hquinolin-2-one bis(trifluoroacetate) and 8-benzyloxy-5-[R-2-[S-(6,7-dihydro-5H-[1]pyridin-6-yl)amino]-1-hydroxyethyl]-1H-quinolin-2-one bis(trifluoroacetate), MH+428.

A suspension of 8-benzyloxy-5-{R-2-[R-(6,7-dihydro-5H-[1]pyrindin-6-yl)amino]-1-hydroxyethyl}-1H-quinolin-2-one trifluoroacetate and 8-benzyloxy-5-{R-2-[S-(6,7-dihydro-5H-[1]pyrindin-6-yl)amino]-1-hydroxyethyl}-1H-quinolin-2-one bis(trifluoroacetate) (22 mg, 0.03 mmol) and 10% Pd/C (10 mg) in ethanol (5 ml) is hydrogenated at 0.35 bar for 1.5 hours. The reaction mixture is filtered, evaporated and purified by preparative LCMS (0-95% acetonitrile water containing 0.1% trifluoroacetic acid gradient) to afford a mixture of 5-{R-2-[R-(6,7-dihydro-5H-[1]pyrindin-6-yl)amino]-1-hydroxyethyl}-8-hydroxy-1H-quinolin-2-one bis(trifluoroacetate) and 5-{R-2-[S-(6,7-dihydro-5H-[1]pyrindin-6-yl)amino]-1-hydroxyethyl}-8-hydroxy-1H-quinolin-2-one bis(trifluoroacetate), MH+338.

Examples 89 to 96

These compounds are prepared using procedures analogous to those used in Example 88 using the appropriate amine.

Example 97

5-{(R)-2-[(R)-1-(6,7-Dihydro-5H-[1]pyrindin-6-ylmethyl)-amino]-1-hydroxy-ethyl}-8-hydroxy-1H-quinolin-2-one bis(trifluoroacetate) salt and 5-{(R)-2-[(S)-1-(6,7-dihydro-5H-[1]pyrindin-6-ylmethyl)-amino]-1-hydroxy-ethyl}-8-hydroxy-1H-quinolin-2-one bis(trifluoroacetate) salt (a) A solution 6,7-dihydro-5H-[1]pyrindine-6-carboxylic acid hydrochloride (Example 88; 0.640 g, 3.21 mmol) and concentrated sulphuric acid (3 drops) in methanol (100 ml) is heated to reflux for 3 hours. The solvent is evaporated, the residue is treated with saturated aqueous $NaHCO_3$ and extracted with EtOAc. The combined organic phases are washed with brine, dried ($MgSO_4$) and evaporated to afford 6,7-dihydro-5H-[1]pyrindine-6-carboxylic acid methyl ester, MH+178.

(b) A solution of 6,7-dihydro-5H-[1]pyrindine-6-carboxylic acid methyl ester (0.450 g, 2.54 mmol) in 7M methanolic ammonia is degassed and heated at 100° C. in a sealed tube for 24 hrs. The solvent is evaporated and the residue purified by flash chromatography (gradient elution 20:1 $CH_2Cl_2$–MeOH–10:1 $CH_2Cl_2$-MeOH–10:1 $CH_2Cl_2$-MeOH+1% triethylamine) to afford 6,7-dihydro5H-[1]pyrindine-6-arboxylic acid amide, MH+163.

(c) 6,7-Dihydro-5H-[1]pyrindine-6-carboxylic acid amide (0.209 g, 1.28 mmol) is added portionwise to a suspension of LiAlH4 (0.204 g, 5.38 mmol) in THF (10 ml). After 5 minutes at ambient temperature, the reaction is heated to reflux for 1.5 hours and then cooled. Water (0.2 ml) is cautiously added, followed by 15% aqueous sodium hydroxide (0.2 ml), followed by further water (0.6 ml). The resultant granular precipitate is filtered and washed with EtOAc. The combined filtrate and washings are evaporated to afford C-(6,7-dihydro-5H-[1]pyrindin-6-yl)methylamine. $\delta_c$ 35.2 (t), 38.9 (t), 41.0 (d), 47.6 (t), 121.6 (d), 132.6 (d), 136.4 (s), 148.1 (s), 164.8 (s).

(d) N,O-bis(trimethylsilyl) acetamide (0.159 ml, 0.64 mmol) is added to a solution of C-(6,7-dihydro-5H-[1]pyrindin-6-yl)methylamine (0.191 g, 1.28 mmol) in DMF (1.2 ml). After 25 mins at ambient temperature, 8-benzyloxy-5-R-oxiranyl-1H-quinolin-2-one (0.252 g, 0.86 mmol) is added and the mixture heated at 100° C. for 28 hours. The solvent is evaporated and the residue taken into methanol (2 ml) and treated with $K_2CO_3$ (0.206 g, 1.49 mmol) with stirring for 1.5 hours. The solvent is evaporated and the residue triturated with water. The residual solid is taken into methanol, treated with decolourising charcoal and filtered through a Celite™ plug. The filtrate is evaporated and purified by preparative LCMS to afford a mixture of 8-benzyloxy-5-{(R)-2-[(R)-1-(6,7-dihydro-5H-[1]pyrindin-6-ylmethyl)-amino]-1-hydroxyethyl}-1H-quinolin-2-one bis(trifluoroacetate) and 8-benzyloxy-5-{(R)-2-[(S)-1-(6,7-dihydro-5H-[1]pyrindin-6-ylmethyl)-amino]-1-hydroxyethyl}-1H-quinolin-2-one bis(trifluoroacetate), MH+442.

(e) A suspension of 8-benzyloxy-5-{(R)-2-[(R)-1-(6,7-dihydro-5H-[1]pyrindin-6-ylmethyl)-amino]-1-hydroxyethyl}-1H-quinolin-2-one bis(trifluoroacetate) and 8-benzyloxy-5-{(R)-2-[(S)-1-(6,7-dihydro-5H-[1]pyrindin-6-ylmethyl)-amino]-1-hydroxyethyl}-1H-quinolin-2-one bis(trifluoroacetate) (26 mg, 0.04 mmol) and 10% Pd/C (18 mg) in ethanol (5 ml) is hydrogenated at 0.35 bar for 4 hrs. The reaction is filtered and the filtrate evaporated to afford 5-{(R)-2-[(6,7-dihydro-5H-[1]pyrindin-6-ylmethyl)-amino]-1-hydroxy-ethyl}-8-hydroxy-1H-quinolin-2-one bis(trifluoroacetate), MH+352.

Examples 98 to 105

These compounds are prepared using procedures analogous to those used in Example 97 using the appropriate amine.

Examples 106 to 109

These compounds are prepared using procedures analogous to those used in Example 88 using the appropriate amine.

Examples 110 to 113

These compounds are prepared using procedures analogous to those used in Example 81, using R-8-benzyloxy-5-oxiranyl-1H-quinolin-2-one and the appropriate amine.

Examples 114 to 116

These compounds are prepared using procedures analogous to those used in Example 85, using R-8-benzyloxy-5-oxiranyl-1H-quinolin-2-one and the appropriate amine.

Examples 117 to 125

These compounds are prepared using procedures analogous to those used in Example 88, using R-8-benzyloxy-5-oxiranyl-1H-quinolin-2-one and the appropriate amine.

Examples 126 to 134

These compounds are prepared using procedures analogous to those used in Example 97, using R-8-benzyloxy-5-oxiranyl-1H-quinolin-2-one and the appropriate amine.

Examples 135 to 138

These compounds are prepared using procedures analogous to those used in Example 88, using R-8-benzyloxy-5-oxiranyl-1H-quinolin-2-one and the appropriate amine.

Especially preferred compounds of formula I include compounds of formula XXXV as hereinbefore defined wherein $R^1$, $R^2$ and T are as shown in Table 5 below, the method of preparation being described hereinafter. All compounds are prepared in the free form. 1H NMR spectra are recorded at 400 MHz in $CDCl_3$ unless otherwise noted. Mass spectra are obtained under electrospray ionisation conditions with LC gradient elution of 5% to 95% acetonitrile-water in the presence of 0.1% formic acid.

TABLE 5

| Ex | $R^1$ | $R^2$ | T | MH+ |
|---|---|---|---|---|
| 139 | —OH | —H | indane-furan structure | 403 |
| 140 | —OH | —H | indane-furan structure | — |
| 141 | —OH | —H | indane-thiophene structure | — |

TABLE 5-continued

| Ex | R¹ | R² | T | MH+ |
|---|---|---|---|---|
| 142 | —OH | —H | (2-methylindan-5-yl)-thiazole | — |
| 143 | —OH | —H | (2-methylindan-5-yl)-pyridin-2-yl | — |
| 144 | —OH | —H | (2-methylindan-5-yl)-pyridin-4-yl | — |
| 145 | —OH | —H | (2-methylindan-5-yl)-5-chlorofuran-2-yl | — |
| 146 | —OH | —H | (2-methylindan-5-yl)-5-ethylthiazol-2-yl | — |
| 147 | —OH | —H | (2-methylindan-4-yl)-2H-tetrazol-2-yl | — |
| 148 | —OH | —H | (2-methyl-4-pyrrol-1-yl-indan-6-yl)-5-methyl-1,3,4-thiadiazol-2-yl | — |
| 149 | —OH | —H | (2-methylindan-5-yl)-benzothiophen-2-yl | — |

TABLE 5-continued
| Ex | R¹ | R² | T | MH+ |
|---|---|---|---|---|
| 150 | —H | —OH | 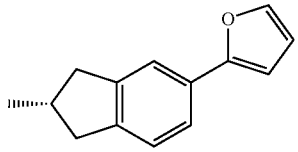 | — |
| 151 | —H | —OH | 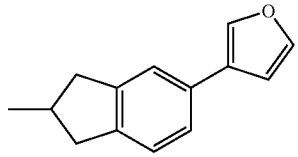 | — |
| 152 | —H | —OH | 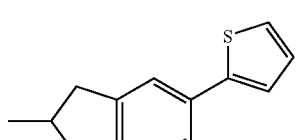 | — |
| 153 | —H | —OH | 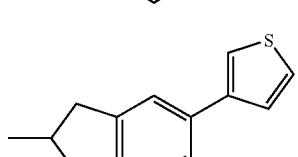 | — |
| 154 | —H | —OH | 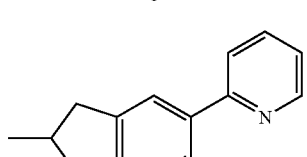 | — |
| 155 | —H | —OH | 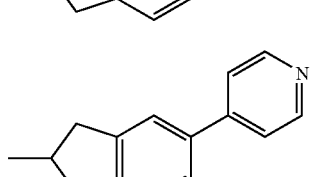 | — |
| 156 | —H | —OH | 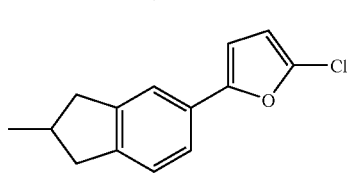 | — |
| 157 | —H | —OH | 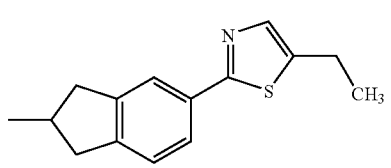 | — |
| 158 | —H | —OH | 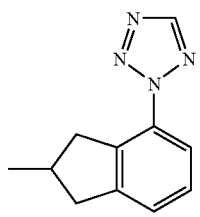 | — |

TABLE 5-continued

| Ex | R¹ | R² | T | MH+ |
|---|---|---|---|---|
| 159 | —H | —OH | (structure: methyl-indane linked to thiadiazole-CH₃, with N-pyrrolyl substituent) | — |
| 160 | —H | —OH | (structure: methyl-indane linked to benzothiophene) | — |

Example 139

5-[R-2-(S-5-(Furan-2-yl)indan-2-ylamino)-1-hydroxyethyl]-8-hydroxy-1H-quinohnl-2-one (a) A solution of (S-5-bromo-indan-2-yl)-carbamic acid tert-butyl ester (WO 9623760, 0.790 g, 2.54 mmol) and 2-(tri n-butylstannyl)furan (0.880 ml, 2.79 mmol) in toluene is degassed by bubbling argon for 5 minutes, then tetrakis(triphenylphosphine)palladium (0.180 g, 0.15 mol) is added and the mixture heated to reflux for 1.5 hours. The solvent is evaporated and the crude product purified by flash chromatography, eluting with 1:1 CH₂Cl₂-isohexane to afford (S-5-(furan-2-yl)indan-2-yl)-carbamic acid tert-butyl ester, MH+ 300.

(b) Trifluoroacetic acid (1.5 ml) is added to a cooled (0° C.) solution of S-5-(furan-2-yl)indan-2-yl)-carbamic acid tert-butyl ester (0.600 g, 2.0 mmol) in CH₂Cl₂ (30 ml). The reaction is warmed to ambient temperature after 1.5 hours, then stirred at ambient temperature for 4.5 hours, prior to re-cooling to 0° C. 1 M NaOH (30 ml) is added, followed by brine and additional CH₂Cl₂. The layers are separated and the organic phase extracted with 0.5 M aqueous HCl. The acidic phase is made basic with 1 M NaOH, extracted with CH₂Cl₂ and the final combined organic phases washed with brine, dried (Na₂SO₄) and evaporated to afford S-5-(furan-2-yl) indan-2-ylamine, MH+200.

(c) Bis(trimethylsilyl)acetamide (72 µl, 0.29 mmol) is added to a solution of S-5-(furan-2-yl)indan-2-ylamine (0.116 g, 0.58 mmol) in N,N-dimethylformamide (D)MF) (1 ml), followed 30 minutes later by 8-benzyloxy-5-R-oxiranyl-1H-quinolin-2-one (0.114 g, 0.389 mmol). The mixture is heated at 85° C. for 48 hours and the solvent is evaporated. The residue is purified by flash column chromatography (Ethyl acetate (EtOAc)-95-5 EtOAc/MeOH-90:10 EtOAc/MeOH gradient elution) to afford 8-benzyloxy-5-[R-2-(S-5-(furan-2-yl)indan-2-ylamino)-1-hydroxyethyl]-1H-quinolin-2-one, MH+494.

(d) A suspension of 8-benzyloxy-5-[R-2-(S-5-(furan-2-yl) indan-2-ylamino)-1-hydroxyethyl]-1H-quinolin-2-one (29 mg, 0.06 mol) and 10% Pd/C (17 mg) in methanol (10 ml) is hydrogenated at 0.35 bar for 45 minutes. The catalyst is removed by filtration and the filtrate evaporated. The residue is triturated with ether and further purified by flash column chromatography (19:1-9:1 CH₂Cl₂/MeOH gradient elution) to afford 5-[R-2-(S-5-(furan-2-yl)indan-2-ylamino)-1-hydroxyethyl]-8-hydroxy-1H-quinolin-2-one, MH+403.

Examples 140 to 149

The compounds of these Examples are prepared analogously to Example 139 using the appropriate carbamic acid tert-butyl ester or amine.

Example 150

5-[R-2-(S-5-(Furan-2-yl)indan-2-ylamino)-1-hydroxyethyl]-7-hydroxy-1H-quinolin-2-one This compound is prepared using procedures that are analogous to those described in Example 139 except using 7-benzyloxy-5-R-oxiranyl-1H-quinolin-2-one in place of 8-benzyloxy-5-R-oxiranyl-1H-quinolin-2-one.

Examples 151 to 160

The compounds of these Examples are prepared using procedures that are analogous to those described in Example 150 using the appropriate carbamic acid tert-butyl ester or amine.

The invention claimed is:

1. A compound of formula I:

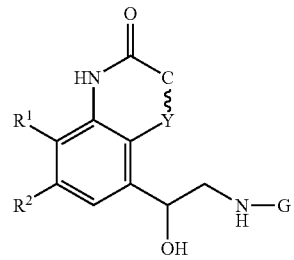

I in free or salt form, where
R$^1$ is hydroxy and R$^2$ is hydrogen;
G is a group having the formula Ib:

C~C denotes C=C or CH—CH;
R$^7$ and R$^8$ are both hydrogen;
R$^9$ and R$^{10}$ are independently selected from the group consisting of hydrogen and C$_1$-C$_{10}$ alkyl, or R$^9$ and R$^{10}$ together form a C$_3$-C$_{10}$ cycloalkyl or C$_3$-C$_{10}$ cycloalkenyl, and in either case wherein R$^9$ and R$^{10}$ are optionally substituted by C$_1$-C$_{10}$ alkyl; and
R$^{11}$ is a C$_3$-C$_{15}$ carbocyclic group or C$_1$-C$_{10}$ alkyl substituted by a C$_3$-C$_{15}$ carbocyclic group.

2. The compound according to claim 1, wherein:
R$^1$ is hydroxy and R$^2$ is hydrogen;
C~C denotes C=C or CH—CH;
R$^7$ and R$^8$ are both hydrogen;
R$^9$ and R$^{10}$ are independently selected from the group consisting of hydrogen or C$_1$-C$_4$ alkyl, or
R$^9$ and R$^{10}$ together form a C$_3$-C$_6$ cycloalkyl or C$_3$-C$_6$ cycloalkenyl, and in either case wherein R$^9$ and R$^{10}$ are optionally substituted by C$_1$-C$_4$ alkyl; and
R$^{11}$ is a C$_3$-C$_{10}$ carbocyclic or C$_1$-C$_{10}$ alkyl substituted by a C$_3$-C$_{10}$ carbocyclic group.

3. The compound according to claim 2, wherein R$^{11}$ is a C$_3$-C$_6$ cycloalkyl.

4. The compound according to claim 2, wherein R$^{11}$ is a C$_1$-C$_{10}$ alkyl substituted by an unsaturated C$_{5-8}$ carbocyclic group.

5. The compound according to claim 1 that is:
5-[R-2-(1S,2S-2-Cyclohexylcyclopentylamino)-1-hydroxyethyl]-8-hydroxy-1H-quinolin-2-one;
5-[R-2-(1R,2R-2-cyclohexylcyclopentylamino)-1-hydroxyethyl]-8-hydroxy-1H-quinolin-2-one;
5-[R-2-(1R,2R-bicyclopentyl-2-ylamino)-1-hydroxyethyl]-8-hydroxy-1H-quinolin-2-one; or
5-[R-2-(1R,2R-2-Benzylcyclopentylamino)-1-hydroxyethyl]-8-hydroxy-1H-quinolin-2-one.

6. A pharmaceutical composition comprising a therapeutically effective amount of a compound according to claim 1.

7. A pharmaceutical composition comprising a therapeutically effective amount of a compound according to claim 1 and at least one pharmaceutically acceptable carrier.

8. A pharmaceutical composition comprising a therapeutically effective amount of a compound according to claim 1 and a therapeutically effective amount of another drug substance selected from the group consisting of an anti-inflammatory, a bronchodilator, an antihistamine, an immunosuppressive and an anti-tussive.

9. A method of treating a patient with obstructive or inflammatory airways disease by administering a therapeutically effective amount of at least one compound according to claim 1.

10. A process for the preparation of a compound of claim 1 in free or salt form comprising:
(A) reacting a compound of formula II:

or a protected form thereof wherein R$^1$ and R$^2$ are as defined in claim 1, with a compound of formula III:

H$_2$N-G    III where G is a group of formula Ib:

or a protected form thereof wherein R$^7$, R$^8$, R$^9$, R$^{10}$ and R$^{11}$ are as defined in claim 1; and
(B) recovering the resultant compound of formula I in free or salt form.

11. A process for the preparation of a compound of claim 1 in free or salt form comprising:
(A) reducing a compound of formula IV:

or a protected form thereof wherein R$^1$, R$^2$ and G are as defined in claim 1, to convert the indicated keto group into —CH(OH); and
(B) recovering the resultant compound of formula I in free or salt form.

12. The method of claim 9 wherein the obstructive or inflammatory airways disease is asthma, adult/acute respiratory distress syndrome, chronic obstructive pulmonary or airways disease, chronic bronchitis or dyspnea associated therewith, emphysema, exacerbation of airways hyperreactivity consequent to other drug therapy, bronchitis or pneumoconiosis.

* * * * *